United States Patent
Chan

(10) Patent No.: US 12,059,372 B2
(45) Date of Patent: Aug. 13, 2024

(54) MACULAR INDENTOR AND METHODS OF USE AND MANUFACTURE THEREOF

(71) Applicant: OPTICGON LLC, Flushing, NY (US)

(72) Inventor: Ian Chan, Flushing, NY (US)

(73) Assignee: OPTICGON LLC, Flushing, NY (US)

( * ) Notice: Subject to any disclaimer, the term of this patent is extended or adjusted under 35 U.S.C. 154(b) by 254 days.

(21) Appl. No.: 17/210,122

(22) Filed: Mar. 23, 2021

(65) Prior Publication Data

US 2021/0290434 A1    Sep. 23, 2021

Related U.S. Application Data

(60) Provisional application No. 62/993,608, filed on Mar. 23, 2020.

(51) Int. Cl.
*A61F 9/007* (2006.01)
*B33Y 80/00* (2015.01)

(52) U.S. Cl.
CPC .......... *A61F 9/00727* (2013.01); *B33Y 80/00* (2014.12); *A61F 2220/0075* (2013.01); *A61F 2230/0004* (2013.01); *A61F 2240/002* (2013.01)

(58) Field of Classification Search
CPC .................................................. A61F 9/00727
See application file for complete search history.

(56) References Cited

U.S. PATENT DOCUMENTS

| | | | |
|---|---|---|---|
| 4,238,482 A | 12/1980 | Peyman et al. | |
| 4,549,529 A | 10/1985 | White | |
| 4,902,292 A | 2/1990 | Joseph | |
| 5,743,274 A | 4/1998 | Peyman | |
| 5,824,073 A | 10/1998 | Peyman | |
| 6,059,828 A | 5/2000 | Peyman | |
| 7,008,396 B1 | 3/2006 | Straub | |
| 2006/0039952 A1 | 2/2006 | Yaacobi | |
| 2010/0004581 A1 | 1/2010 | Brigatti et al. | |
| 2014/0074234 A1 | 3/2014 | Reus et al. | |
| 2014/0180411 A1 | 6/2014 | Tornambe et al. | |

(Continued)

FOREIGN PATENT DOCUMENTS

| | | | |
|---|---|---|---|
| CN | 108066054 A | * | 5/2018 |
| CN | 109661194 A | | 4/2019 |
| CN | 110403755 A | | 11/2019 |

(Continued)

OTHER PUBLICATIONS

Aironi, V. et al., "Pictorial essay: B-scan ultrasonography in ocular abnormalities" Indian J Radiol Imaging. May 2009 ; 19(2): 109-115.

(Continued)

*Primary Examiner* — Javier G Blanco
(74) *Attorney, Agent, or Firm* — DUANE MORRIS LLP

(57) ABSTRACT

A macular indentor for implantation on an eye of a patient includes a curved backbone extending from a first end to a second end and a raised pad coupled to the first end of the backbone. The raised pad extends inward from an inner face of the backbone such that, when the macular indentor is implanted on the eye, the raised pad applies pressure to the sclera of the eye which contacts the macula of the eye. The geometry of the backbone is configured to match the geometry of the eye.

6 Claims, 24 Drawing Sheets
(19 of 24 Drawing Sheet(s) Filed in Color)

(56) References Cited

U.S. PATENT DOCUMENTS

2014/0268036 A1  9/2014  Ketterling et al.
2018/0018515 A1  1/2018  Spizhevoy et al.

FOREIGN PATENT DOCUMENTS

SU         1537274 A  *  1/1990
WO      2017033081 A2     3/2017

OTHER PUBLICATIONS

Ando et al., "Use of a special macular eplant in surgery for retinal detachment with macular hole." Jpn J Ophthalmol 1980;24:29-34.
Bücking, et al., "From medical imaging data to 3D printed anatomical models", PLoS One. May 2017; 12(5): e0178540. 10 pages.
Cacciamani, et al. "Adjustable macular buckling for full-thickness macular hole with foveoschisis in highly myopic eyes: Long-term anatomical and functional results", Retina. Apr. 2016; 36(4):709-716.
Devin, et al., "T-shaped scleral buckle for macular detachments in high myopes", Retina. Jan. 2011;31(1):177-180.
Grewal, et al., "Macular buckle without vitrectomy for myopic macular schisis: A Canadian case series", Can J Ophthalmol. Feb. 2019; 54(1):60-64.
Juneja, et al., "Accuracy in dental surgical guide fabrication using different 3-D printing techniques", Additive Manufacturing. May 2018; 22: 243-255.
Liu, et al., "Macular buckling using a three-armed silicone capsule for foveoschisis associated with high myopia", Retina. Oct. 2016; 36(10): 1919-26.
Mateo, et al., "Illuminated Ando plombe for optimal positioning in highly myopic eyes with vitreoretinal diseases secondary to posterior staphyloma", JAMA Ophthalmol. Oct. 2013; 131(10):1359-62.
Mura, et al., "T-shaped macular buckling combined with 25G pars plana vitrectomy for macular hole, macular schisis and macular detachment in highly myopic eyes", Br J Ophthalmology. Mar. 2017; 101(3): 383-388.
Rosengren, "The silver plomb method in macular holes", Trans Ophthalmol Soc UK. 1966; 86:49-53.
Schepens, et al., "The scleral buckling procedures. I. Surgical techniques and management" AMA Arch. Opthalmol. Dec. 1957; 58(6):797-811.
Siam, et al., "Macular buckling for myopic macular hole retinal detachment: A new approach", Retina. Apr. 2012; 32(4): 748-753.
Sun, et al., "Combined Vitrectomy with Macular Buckling in High Myopic Eyes with Macular Hole Retinal Detachment: A Pilot Study of a Novel Snail-Tipped Exoplant", Clin Ophthalmol. Nov. 2019: 13: 2233-2242.
Susvar, et al., "Current concepts of macular buckle in myopic traction maculopathy", Indian J Ophthalmol. Dec. 2018; 66(12): 1772-1784.
Theodossiadis, "A simplified technique for the surgical treatment of retinal detachment resulting from macular holes", in Monbl Augenheilkd 1973;162:719-28 (Abstract Only).
International Search Report and Written Opinion for PCT/US2021/023714 dated Jul. 1, 2021, 20 pages.
Extended European Search Report in EP Application No. 21775351.6, dated May 24, 2024, in 7 pages.
Search report from Office Action in Chinese Counterpart Application No. 2021800371438 dated May 1, 2024 in 4 pages.

* cited by examiner

Red circle
Orange circle

Green circle

MACULAR INDENTOR AND METHODS OF USE AND MANUFACTURE THEREOF

PRIOR RELATED APPLICATION

This application claims priority to U.S. Provisional Application Ser. No. 62/993,608, filed Mar. 23, 2020, the contents of which are herein incorporated in its entirety.

FIELD

This disclosure relates to the field of ophthalmological surgery devices. In particular, this disclosure relates to macular buckles, methods of their making based on a patient's specific ocular image features, and methods of their insertion to the eye of a patient.

BACKGROUND

The following includes information that may be useful in understanding the present invention. It is not an admission that any of the information, publications or documents specifically or implicitly referenced herein is prior art, or essential, to the presently described or claimed inventions. All publications and patents mentioned herein are hereby incorporated herein by reference in their entirety.

Multiple macular indentors or "macular buckles" as they are known in the retina surgery community have been previously proposed and used in clinical studies. The earliest macular buckle was developed in 1957 by Dr. Charles Schepens and described in Schepens C L et al., *The scleral buckling procedures. I. Surgical techniques and management*, AMA Arch. Opthalmol., 1957; 58:797-811. Modifications to these macular buckles were made by Rosengren and Theodonsiadis and described in Rosengren B., *The silver plomb method in macular holes*, Trans Ophthalmol Soc UK 1966; 86:49-53 and Theodossiadis G P, *A simplified technique for the surgical treatment of retinal detachment resulting from macular holes*, Lin Monbl Augenheilkd 1973; 162:719-28, respectively. More contemporary versions of macular buckles include suture adjustable positioning, fiber optic verification of position, bendable backbone as well as different geometries and materials. These macular buckles have demonstrated the safety and efficacy of the concept of macular indentation to treat various macular diseases for myopic patients including myopic tranctional maculopathy, macular hole, macular schisis and retinal detachments.

All of the previous concepts in macular buckles involve a one-size-fit-all design concept with some allowing minor adjustment to be made on the fly during surgery. Due to the high amount of variability in the shape, length, and curvature of highly myopic eyes, these one-size-fit-all designs can fit poorly when implanted, cause stability issues, and the accuracy of the placement over the macula region may be inaccurate. Also, in current designs, adjustments made to the device and its placement are highly surgeon-dependent. Further, the device may move after visualization and suturing of the device to the sclera. Long term positional stability of the device is also a concern as the suture may be too lax and the device may slide in different directions after placement. Due to the high level of variations in shape, length and sizes of highly myopic eyes, correct positioning of the device to support the macula is a challenge. These factors lead to variable clinical outcomes for individuals having macular buckle surgeries.

Additive manufacturing can produce end-use components which generally exhibit high geometric configurations and configured applications, including implantable medical devices. At least some known additive manufacturing (AM) processes encompass a variety of forms to cover an entire range of quick-response direct fabrication, typically in a layered format with unprecedented design freedom. AM generally enables the creation of geometries that can be very difficult to machine.

At least some known component geometries can be designed according to the manufacturing method that can be used to machine the final component. At least some known standard computer-aided engineering and design (CAD) tools that are used to produce three-dimensional (3D) models can mimic standard machine shop methods when designing a 3D model to ensure that the components will be manufacturable using standard methods at a reasonable cost.

SUMMARY

The embodiments described herein have many attributes and aspects including, but not limited to, those set forth or described or referenced in this Summary. It is not intended to be all-inclusive and the embodiments described herein are not limited to or by the features or embodiments identified in this Summary, which is included for purposes of illustration only and not restriction.

In one aspect, a macular indentor for implantation on an eye of a patient is disclosed. The macular indentor includes a curved backbone extending from a first end to a second end and a raised pad coupled to the first end of the backbone. The raised pad extends inward from an inner face of the backbone such that, when the macular indentor is implanted on the eye, the raised pad applies pressure to the sclera of the eye which contacts the macula of the eye. The geometry of the backbone is configured to match the geometry of the eye by the methods described herein. The fit of the macular indentor to the eye can be confirmed using OCT (optical coherence tomography) imaging of the retina.

In another aspect, this disclosure provides for a method of treating a patient having an ocular condition, the method comprising attaching a macular indentor described herein to the eyeball of the patient. In some aspects, the attachment occurs by suturing. In some aspects, the attachment occurs by contacting a portion or all of the macular indentor with a surgical glue, then contacting the macular indentor to the eyeball and allowing the glue to set. In some aspects, the surgical glue is selected from: ReSure Sealant (polyethylene glycol and trilysine acetate), cyanoacrylate, fibrin glue, Duraseal (polyethylene glycol ester and trilysine), Focalseal (polyethylene glycol acrylate and photoinitiator, cured by blue light), L-β-3,4-dihydroxyphenyl-α-alanine (DOPA), chondroitin sulfate reacting with glycidyl methacrylate, Bio-Glue (bovine albumin and glutaraldehyde), Progel (human albumin and a PEG crosslinker with two NHS activated ester groups), fibrin (Tisseel (Baxter Inc., Denmark), Evicel (Ethicon Inc., Bridgewater, NJ), Crosseal (OMRIX Biopharmaceuticals Ltd. Israel), and Hemaseel (Heamacure Corp., Canada)), Coseal (Cohesion Technologies, Inc., Palo Alto, CA) (PEG-based sealant, which is made of two 4-arm PEG with glutaryl-succinimidyl ester and thiol terminal groups), FocalSeal, and AdvaSeal (Ethicon Inc., Johnson & Johnson Medical KK). In some aspects, the ocular condition is selected from: myopic tractional maculopathy, macular hole, myopic foveoschisis, myopic tractional maculopathy, posterior staphyloma and macular hole with retinal detachment. In some aspects, the method further comprises confirming the proper placement of the macular indentor on the eyeball. The placement of the macular indentor can be confirmed with the use of a fiber optic which is removably attached to the backbone of the macular indentor (e.g., via sutures), and the fiber optic is configured to emit light at the tip of the fiber optic and detected by indirect ophthalmoscope during surgery. The fiber optic can be pulled to extract the fiber optic after implantation of the macular indentor.

In some aspects, this disclosure provides for the use of a macular indentor described herein for treating a macular disease in a patient by surgically suturing the macular indentor to the eyeball of said patient.

In another aspect, a method includes receiving a first image of an eye of a patient. The method further includes delineating the outline of a globe of the eye. The method further includes developing a curve that matches the outline of the globe of the eye. The method further includes generating geometry of a macular indentor such that a portion of the macular indentor follows the curve that matches the outline of the globe of the eye.

In another aspect, a system for designing and manufacturing by additive manufacturing methods a patient-specific macular indentor is disclosed. The system comprises: (a) a computer unit which receives a first image of an eye of a patient, delineates the outline of a globe of the eye, develops a curve that matches the outline of the globe of the eye, and generates a geometry of a macular indentor such that a portion of the macular indentor follows the curve that matches the outline of the globe of the eye, and (b) an additive manufacturing device which creates an additively-manufactured macular indentor matching the generated geometry.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The drawings form part of the present specification and are included to further demonstrate certain aspects of the embodiments described herein. These embodiments may be better understood by reference to one or more of the following drawings in combination with the detailed description.

FIG. 4A-FIG. 4D show various B-scan ultrasonographic orientations; wherein FIG. 4A shows axial orientation and FIG. 4B shows transverse orientation, FIG. 4C shows a longitudinal orientation. FIG. 4D shows an angular orientation.

DETAILED DESCRIPTION

Figure 1A:
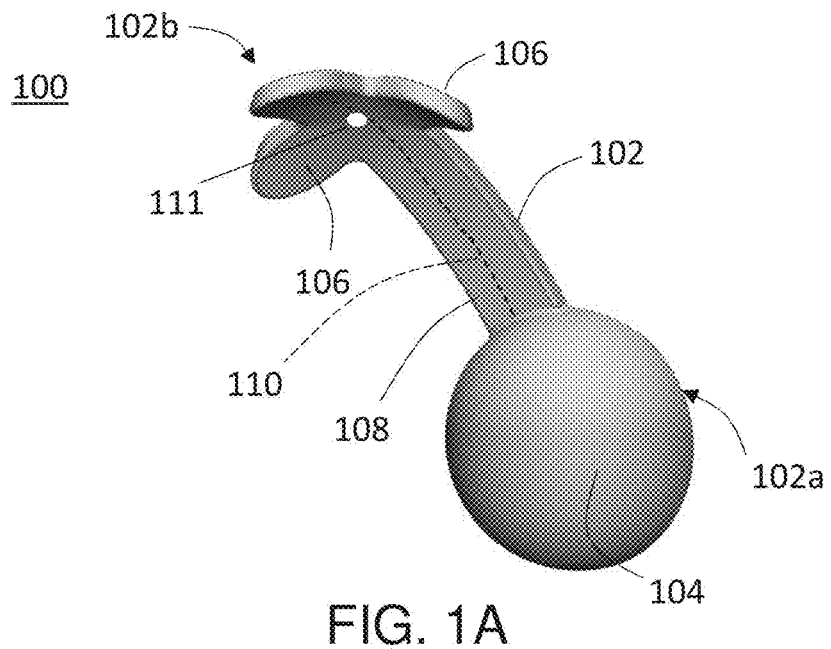
FIG. 1A is a perspective view of a macular indentor according to embodiments described herein.
Figure 1B:
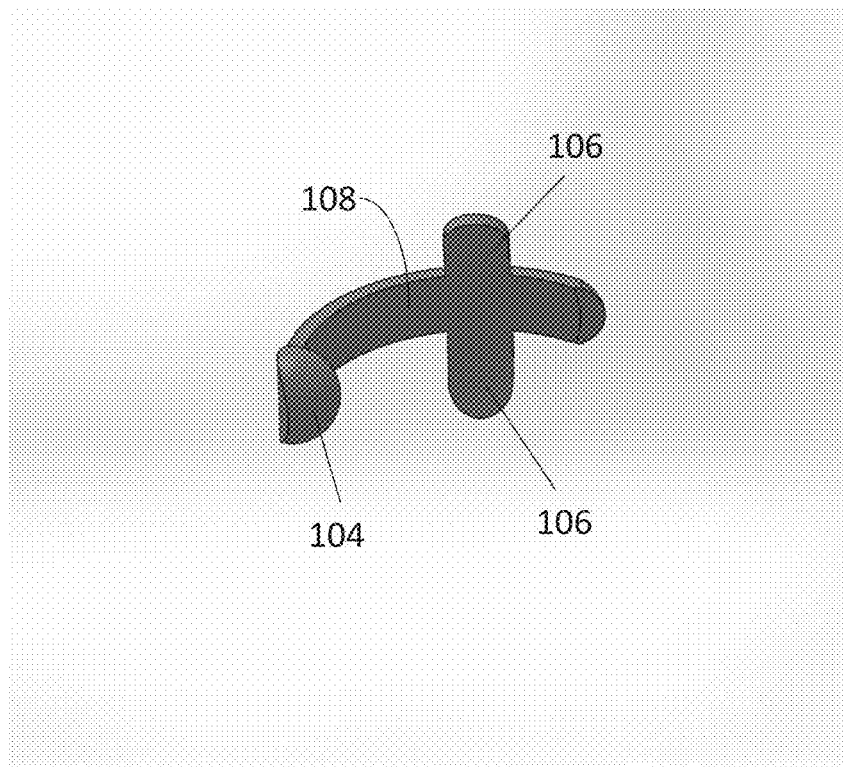
FIG. 1B is a bottom view of a macular indentor according to embodiments described herein.
Figure 1C:
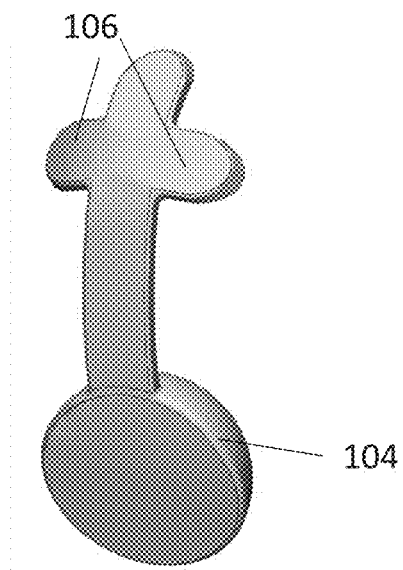
FIG. 1C is a top perspective view of a macular indentor according to embodiments described herein.
Figure 1D:
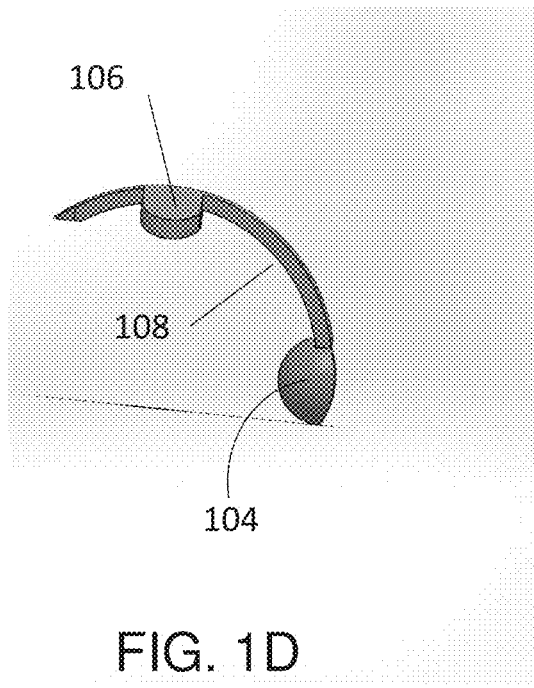
FIG. 1D is a side view of a macular indentor according to embodiments described herein.
Figure 1E:
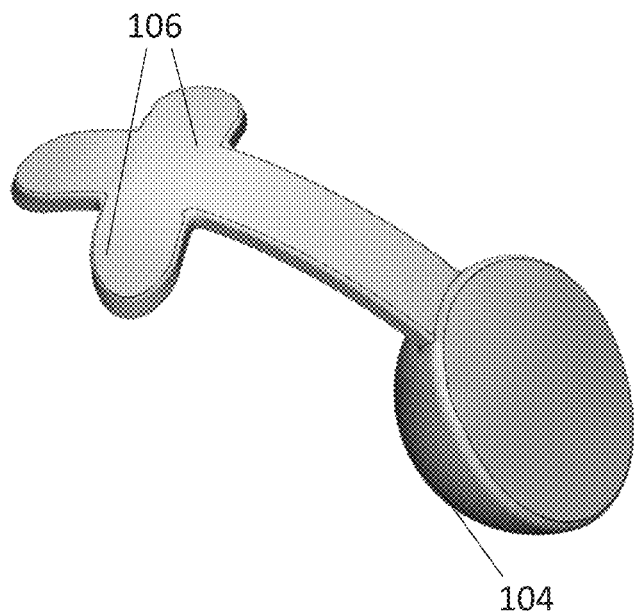
FIG. 1E is an alternative top perspective view of a macular indentor according to embodiments described herein.
Figure 1F:
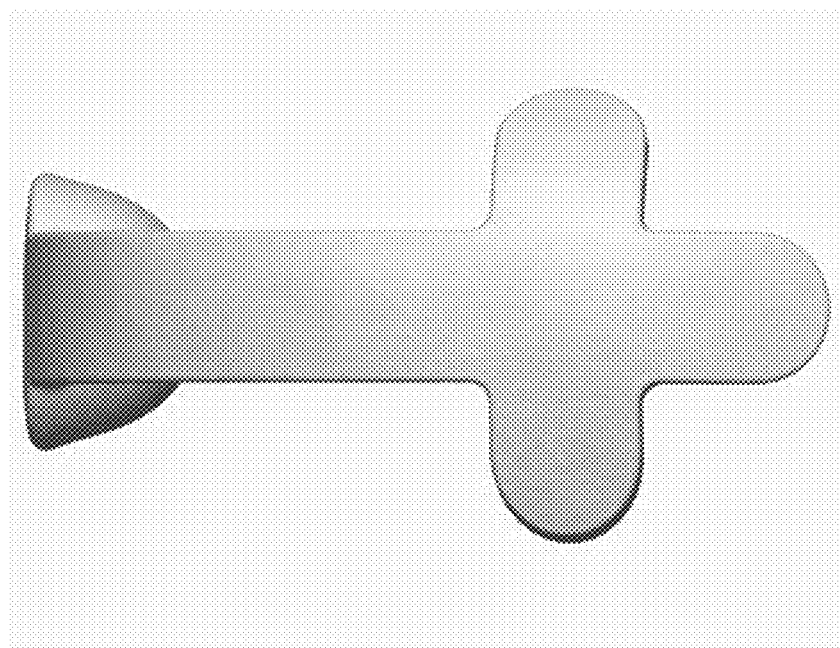
FIG. 1F is a top view of a macular indentor according to embodiments described herein.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

As used herein, ocular directionality terms such as "superior", "inferior", "temporal", and "nasal" are understood to have their normal meaning in the art and refer to the relative positions of the eyeball.

Macular Indentors

The present disclosure is related to macular indentors used in macular buckling surgeries to treat pathologies including myopic tractional maculopathy, macular hole, myopic foveoschisis, myopic tractional maculopathy, posterior staphyloma and macular hole with retinal detachment. The macular indentors described herein are configured to fit to a specific patient's eye geometry to improve the positioning and retention of the indentor. The fact that the macular indentor is configured to fit to the patient's eye geometry allows for the inclusion of additional retention features to provide additional support to retain the indentor in place. This description also discloses methods of designing and manufacturing such indentors.

The indentors described herein may support the macula from the scleral side of the eye by creating an indentation of the macula. The indentor may be formed using additive manufacturing (e.g., 3D printing) and may be configured to fit the curvature, shape, length and size of the individual eye being treated. The geometry of the indentor may be determined using image guidance from Bscan ultrasonography, A-scan ultrasonography, 3D ultrasounds, and/or ocular coherence tomography.

Additive manufacturing the indentor based on the eye geometry allows for improved accuracy in placement and increased stability of the device. The configured geometry of the indentor may also decrease inter-surgeon variability on results of the surgery (i.e., dependency on surgical skill). Because the geometry of the macular indentors described herein may be configured designed to fit to the patient's eye, the device may fit smoothly along the sclera and follow the natural curvature of the individual eye. Like a foot orthotic or a dental implant that is configured to fit the geometric shape of the appropriate portion of the patient, the placement of the indentor is more repeatable than with prior art indentors, thereby reducing the variability on the outcome of the surgery based on the skill of the surgeon. The configured sizing of the indentor also increases the likelihood that the indentor is correctly positioned. Further, such an indentor may increase the long term positional stability of the indentor, reducing the risk of slippage or extrusion after implantation.

In one embodiment, a macular indentor for implantation on an eye of a patient is disclosed. The macular indentor includes a curved backbone extending from a first end to a second end and a raised pad coupled to the first end of the backbone. The raised pad extends inward from an inner face of the backbone such that, when the macular indentor is implanted on the eye, the raised pad applies pressure to the sclera of the eye which contacts the macula of the eye. In some embodiments, the sclera of the eye to which the pad applies pressure to is adjacent to the macula of the eye. In some embodiments, the sclera of the eye to which the pad applies pressure to ranges from 0 to 2 mm of the macula of the eye. The geometry of the backbone is configured to match the geometry of the eye by the methods described herein.

In some embodiments, the macular indentor further comprises at least one arm extending from the second end of the backbone, wherein the arm is configured to match the geometry of the eye. The configuration of the multiple arms can be situated such that a leverage is applied against the peripheral outline of the eyeball so as to keep the bulb positioned in the same location despite movement of the eyeball. In some embodiments, the at least one arms extends orthogonally to a mid-line of the backbone. In some embodiments, when there are two or more arms, they can be configured to be from 5 to 180 degrees from each other. In some embodiments, the at least one arm can comprise two arms extending from the backbone in opposite directions such that the arms and the backbone form a cross shape.

In some embodiments, the macular indentor further comprises at least one aperture which is configured to receive a suture to secure the macular indentor to the eye. The aperture can be of a shape selected from round, oval, polygon (wherein the polygon has from 3 to 20 sides), or multipoint star-shaped (wherein the star has from 4 to 64 points). In some embodiments, the macular indentor can comprise one or a plurality of apertures extending through said indentor. In some embodiments, at least one of the apertures is positioned at the intersection of the arms and the midline of said indentor.

In some embodiments, the thickness of the raised pad (also referred to herein as the "bulb") can be configured based on a macular detachment height, and can range from 0.3 mm to 5 mm. In some embodiments, the width of the backbone and/or arms can range from 2 mm to 7 mm. In some embodiments, the thickness of the backbone and/or arms can range from 0.2 mm to 4.5 mm.

In some embodiments, the cross-section of the raised pad can be semi-spherical and can be configured to create a semi-spherical indentation of the macula. In some embodiments, the cross-section of the raised pad is semi-oval (selected from length-wise or width-wise) and can be configured to create a semi-oval indentation of the macula. In some embodiments, the cross-section of the raised pad can be a parallelogram and be configured to create a flat indention of the macula.

In some embodiments, the macular indentor is constructed from at least one material selected from the group consisting of: titanium, cobalt, nylon, Teflon (polytetrafluoroethylene), polyurethane, high density polyethylene (HDPE), polypropylene, and stainless steel. In some embodiments, the macular indentor is created byh a process comprising additive-layered manufacturing (also referred to herein as "3D printing"). In some embodiments, the macular indentor can be coated with a silicone covering.

One embodiment of an indentor 100 is shown in FIG. 1. The indentor 100 includes a backbone 102 and a raised pad 104 at a first end 102a of the backbone 100. In some embodiments, the indentor 100 may further include one or more arms 106 extending from the backbone 100. As described herein, the backbone 102, the raised pad 104 and the arms 106 may be dimensioned to fit the geometry of a specific patient's eye, thereby increasing the reliability of the placement of the indentor 100 and minimizing the risk of movement of the indentor 100 after implantation.

The backbone 102 extends from the first end 102a to a second end 102b and extends along a curved path. The curvature and length of the backbone 102 is determined based on the geometry of the eye to which the indentor 100 is to be affixed, as described further herein. The backbone 102 includes an inner face 108 that is configured to be positioned against the eye (e.g., against the sclera).

As noted above, the raised pad 104 is coupled to the first end 102a of the backbone 102. As described further herein, in some embodiments, the backbone 102 and raised pad 104 are formed together—for example, using an additive manufacturing process. In other embodiments, the backbone 102 and the raised pad 104 may be joined using adhesive, welding, or other methods. The raised pad 104 may be substantially circular in cross-section and may protrude inward from the inner face 108 of the backbone 102 such that, when the indentor 100 is implanted, the raised pad 104 extends inward toward the macula to apply localized pressure on the eye. The raised pad 104 may be, for example, dome shaped. The amount that the raised pad 104 extends inward from the inner face 108 of the backbone 102 can be determined based on the amount of pressure that the surgeon wishes to apply to the eye to treat the pathology and the geometry of the eye (as determined based on images captured as described herein).

The arms 106 may extend from the second end 102b of the backbone 102. In some embodiments, the indentor 100 includes two arms 106 extending from the backbone 102 and away from one another. In some embodiments, the indentor 100 includes a plurality of arms 106 extending from the backbone 102, wherein the number of arms can be one to eight. In some embodiments, the arms 106 extend orthogonally to a midline 110 of the backbone 102, as shown in FIG. 1. In some embodiments, the arms can extend at an angle ranging from 1 to 90 degrees from the a midline of the backbone. The midline 110 follows the curvature of the backbone 102 from the first end 102a to the second end 102b. In other embodiments, the arms 106 extend at obtuse angles relative to the midline 110. With the arms 106 extending orthogonally to the midline 110, the indentor 100 may take on the shape of a cross at the second end 102b of the backbone 102. The arms 106 enhance the stability of the indentor 100 when implanted by increasing the contact with the eye, particularly around the circumference of the eye. Manufacturing the indentor 100 to be specific to a given patient allows for inclusion of the arms 106. Ensuring proper sizing and geometry of the arms 106 may not be possible with standard indentors because of the variability of myopic eye geometry. In various embodiments, the arms 106 may include apertures 111 extending therethrough to receive a suture to secure the indentor 100 to the eye. In some embodiments, at least one aperture is positioned to be at the intersection of the arms and the midline. In some embodiments, the edge of the arms 106 is defined by orthogonal planes so as to be a "square" shape. In some embodiments, the edge of the arms 106 is defined by planes at an angle from 1 to 89 degrees so as to be a "parallelogram" shape In some embodiments, the edge of the arms 106 is defined by an oval or circular surface, so as to be a "round" shape.

Figure 2:
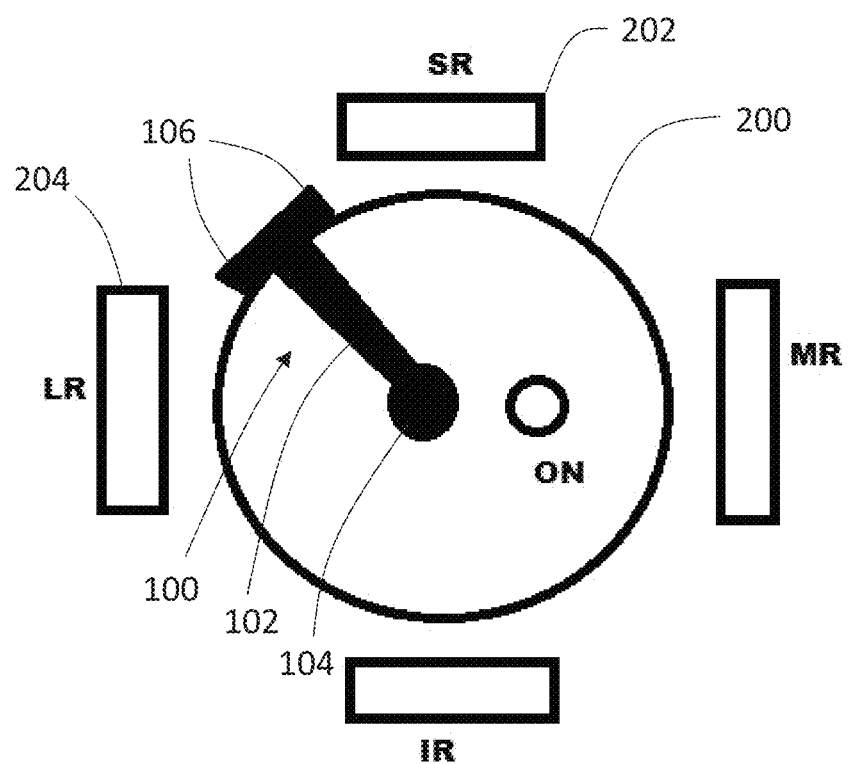
FIG. 2 is a posterior view of a right eye with a macular indentor according to embodiments described herein in place on the eye.

FIG. 2 shows an exemplary placement of the indentor 100 on an eye 200 of a patient. The arms 106 are positioned from 0 to 2 mm from the equator along the equator of the eye. The indentor 100 may be positioned along the equator of the eye 200 midway between the superior rectus muscle 202 and the lateral rectus muscle 204 in the superotemporal quadrant and the backbone 102 may extend at a 45 degree angle such that the raised pad 104 is located at the macula region in the posterior portion of the eye. Although FIG. 2 illustrates an exemplary placement of the indentor 100, it should be understood that the indentor 100 may be oriented and positioned differently than is illustrated. The exact positioning may be based on the eye anatomy, the patient's pathology, and surgeon preference. In some embodiments, the indentor 100 can be placed at the inferotemporal quadrant of the eye. In some embodiments, when there are other pathology and/or glaucoma drainage implants at the superotemporal quadrant, the indentor 100 can be placed along the inferotemporal 45 degree axis. The indentor 100, however, cannot be placed in the nasal quadrants due to optic nerve and other anatomical structures.

The indentor 100 may be sutured to the sclera—for example, with a mattress or X stitch—at various points including, for example, at the arms 106 or along the backbone 102 of the indentor 100. The sutures may help retain the indentor 100 in position and prevent movement after implantation. In some embodiments, a permanent suture may be used to secure the backbone 102 to the sclera. In various embodiments, the indentor 100 may be completely explantable in case of infection or incorrect positioning.

The indentor 100 may be constructed of any appropriate material. For example, the indentor 100 may be constructed of a medical grade implant material such as, for example, titanium, cobalt, stainless steel or plastic (e.g., nylon). In some embodiments, the indentor 100 is constructed from polyurethane (e.g., by additive manufacturing). Constructing the indentor 100 of a material that can be used in an additive manufacturing process allows the indentor 100 to be manufactured quickly after imaging and prior to surgery. Further, the indentor 100 may include a silicone covering. The covering may be applied after forming the indentor 100 via additive manufacturing, for example. In various embodiments, the indentor 100 may be constructed of a material that is sterilizable. In some embodiments, the indentor is made of a material selected from: titanium, nickel-titanium alloy (nitinol), gold, platinum, silver, iridium, tantalum, tungsten, cobalt, cobalt-chrome alloy, nylon, Teflon (polytetrafluoroethylene), polyurethane, high density polyethylene (HDPE), polypropylene, and stainless steel.

Methods of Measuring and Constructing a Macular Indentor Configured to Fit to the Eyeball of a Patient In another embodiment, this disclosure provides for a method for generating a simulated geometry of a macular indentor specific to a measured eyeball of a patient, comprising: receiving a first image of an eye of a patient; delineating the outline of a globe of the eye; developing a curve that matches the outline of the globe of the eye; and generating geometry of a macular indentor such that a portion of the macular indentor follows the curve that matches the outline of the globe of the eye from a range of 0 to 2 mm at any point along the outline of the globe of the eye.

In some embodiments, the first image can be selected from an axial B-scan ultrasonography image or an axial A-scan ultrasonography image. In some embodiments, a plurality of images can be obtained of the eye, wherein the images are from the same imaging technique or different imaging techniques, and wherein the images are from the same direction or different directions. When the imaging is from different directions, the angle by which the two or more directions can vary from a range of 1 degree to 45 degrees.

In some embodiments, the method can comprise receiving a second image of the eye of the patient. The second image can be selected from a transverse B-scan ultrasonography image and/or an A-scan ultrasonography image. In some embodiments, the first and second images can be from the same imaging type or different imaging types. In some embodiments, the method can further comprise developing a second curve based on the outline of the globe of the eye in the second image.

In some embodiments, the method can further comprise receiving a third image of the eye of the patient, wherein the third image is an A-scan ultrasonography image, and wherein the length of the macular indentor is determined based on the third image.

In some embodiments, developing the curve can comprise identifying boundary points on the globe of the eye and fitting the curve to the boundary points.

In some embodiments, fitting the curve can comprise cubic spline interpolation.

In some embodiments, the method can further comprise receiving a fourth image of the eye of the patient, wherein the fourth image is an optical coherence tomography image showing a macular detachment, and wherein the thickness of the pad is determined, at least partially, based on a height of the macular detachment.

In some embodiments, the method can further comprise obtaining an optical coherence tomography image of the eye, and determining the size of a raised pad of the macular indentor based on a height of the macular elevation or detachment on the optical coherence tomography image.

In some embodiments, the method can further comprise forming the macular indentor using additive manufacturing.

Methods of designing and manufacturing an indentor 100 according to the embodiments described above will now be described. Images of the eye to which the indentor 100 will be affixed may be generated in order to allow the indentor 100 to be configured to the anatomy of the patient's eye.

Figure 4:
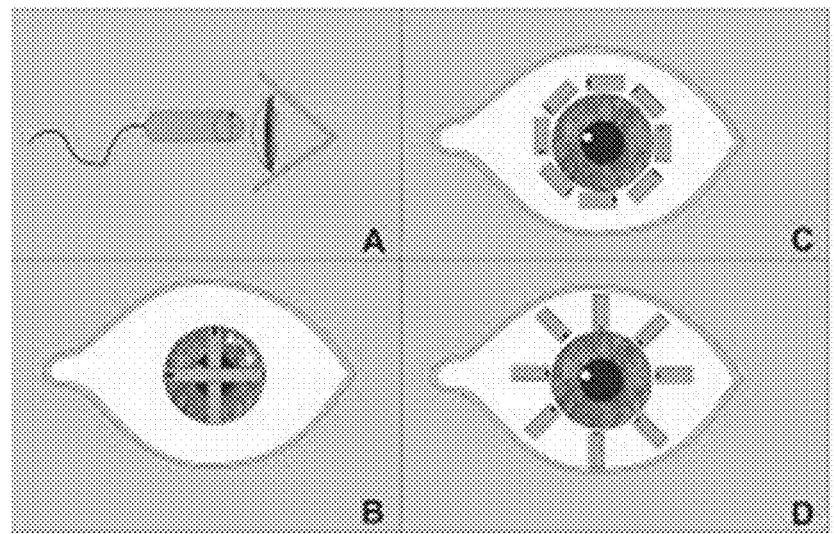
Figure 5:
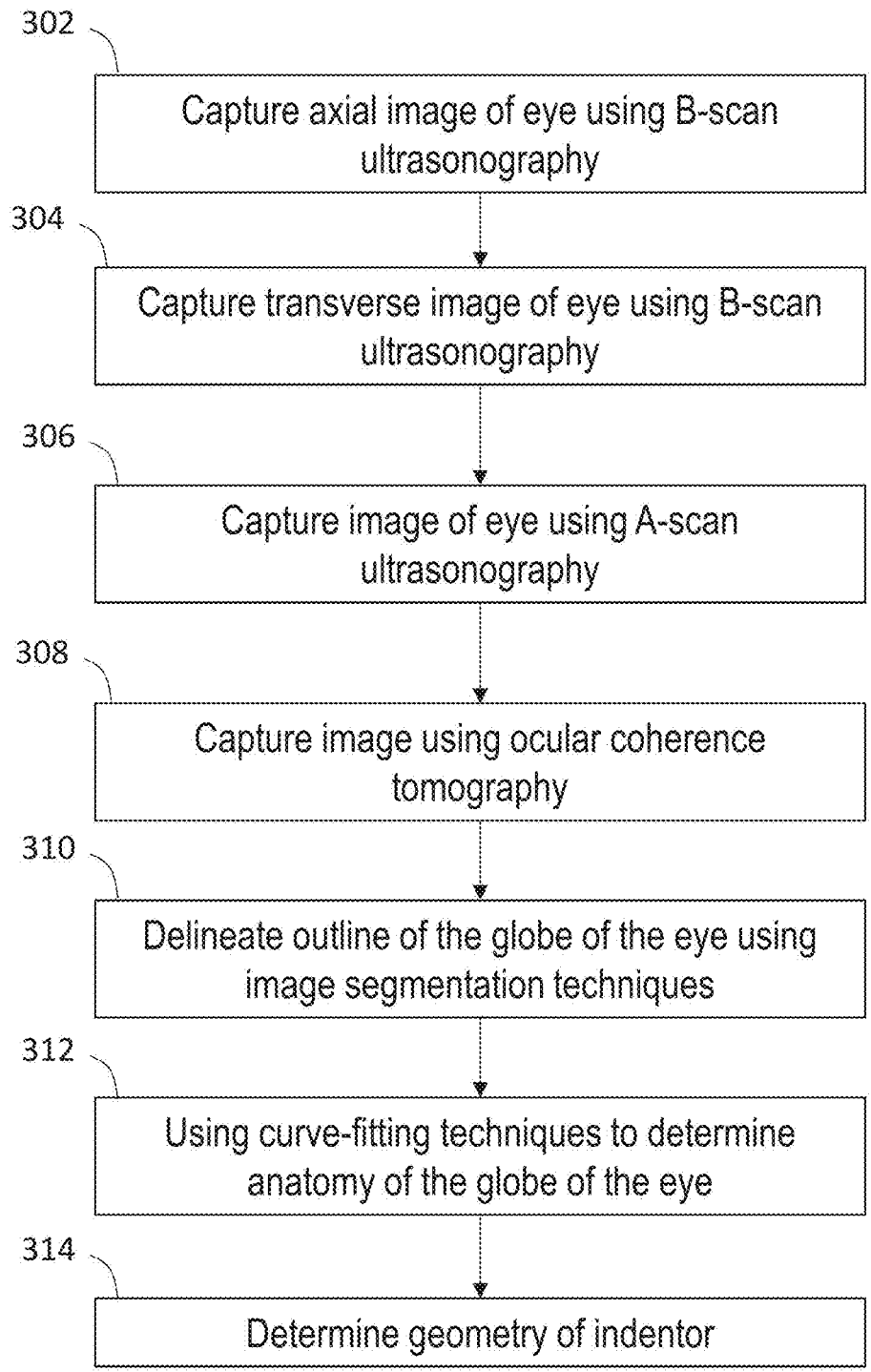
FIG. 5 is a flowchart illustrating a method of determining a geometry of a macular indentor by particular embodiments described herein.

One embodiment of a method of determining a geometry of an indentor is illustrated by the flowchart in FIG. 5. At step 302, B-scan ultrasonography is performed to capture an axial image of the patient's eye. For example, B-scan ultrasonography images may be taken along the 45 degree meridian, which is the axis of the intended implantation. FIGS. 4A and 4B illustrate an arrangement for an obtaining an axial B-scan image. Based on such images, the curvature of the patient's sclera along the superotemporal quadrant can be obtained. As described in further detail below, curve-fitting techniques—such as, for example, spline curve fitting and curve interpolation—may be used to determine the curvature of the backbone 102 of the indentor 100 such that it closely follows the shape of the eye. The geometry of the eye may be determined by using multiple point curve interpolation. This may allow for the identification of complex curvatures of a highly myopic eye that does not follow a spherical or oval shape.

As used herein, the term "B-scan ultrasonography" refers to an ultrasonic-based imaging system to obtain structural ocular features. Representative examples of B-scan ultrasonography are further discussed in Aironi, V. et al, Indian J Radiol Imaging. 2009 May; 19(2): 109-115, the contents of which are herein incorporated by reference.

At step 304, transverse images of the eye are acquired using B-scan ultrasonography (brightness scan ultrasonography) at the equator of the eye. FIG. 4C illustrates an arrangement for obtaining a transverse B-scan image. The transverse B-scan images can be used to determine the optimal transverse curvature of the arms 106 of the indentor 100. As described herein, based on the transverse images of the eye, curve fitting techniques (e.g., splint and polynomial curve interpolation) can be used to determine the optimal geometry of the arms 106 such that they follow the transverse curvature of the eye.

At optional step 306, images of the eye may be captured using A-scan ultrasonography (i.e., amplitude scan ultrasonography). These images can be used to determine the length of the eye, and/or confirm the transverse images obtained from B-scan imaging. The information regarding the length of the eye can be used to determine an optimum length of the indentor 100 (e.g., the backbone 102). In some embodiments, no A-scan imaging is performed.

Figure 3:
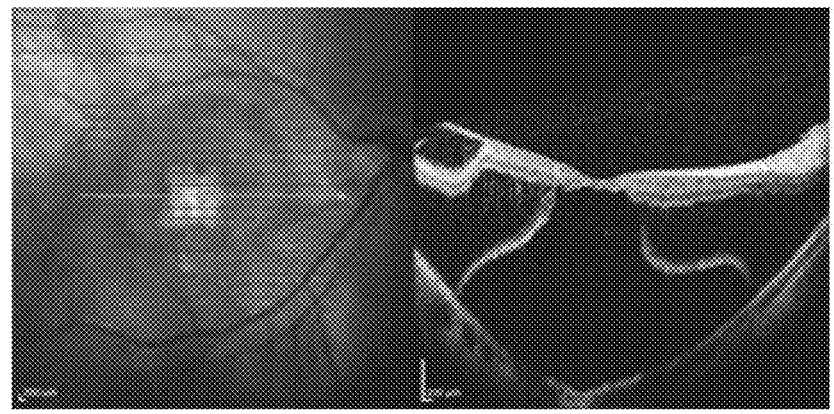
FIG. 3 shows an eye having a myopic tractional maculopathy and an ocular coherence tomography image showing macula detachment.

At optional step 308, images of the eye may be acquired using ocular coherence tomography. An exemplary image is provided in FIG. 3. These images can be used to determine the height of the macular detachment. The thickness of the raised pad 104 of the indentor 100 (i.e., the extent to which the raised pad 104 extends inward from the inner face 108 of the backbone 102) can be determined based on the macular detachment height. For example, the thickness of the raised pad 104 may be greater for patients having greater macular elevation. In some embodiments, no ocular coherence tomography is performed.

It should be understood that other imaging modalities can optionally be used to determine the geometry of the eye and/or confirm the eye measurements from the aforementioned modalities. For example, 3D ultrasound images can be used to determine geometry information for the entire globe structure (as compared to slices obtained using 2D ultrasound). Using 3D ultrasound may be used in addition to the imaging modalities described above or may be used in substitution for one or more of the above-described imaging modalities.

At step 310, the outline of the globe of the eye in the B-scan ultrasonography images is delineated using image segmentation techniques. The image segmentation may be performed manually—for example, by the surgeon or designee—or may be performed automatically using computer-implemented methods. As used herein, the term "image segmentation" refers to the process of partitioning a digital image into multiple segments (sets of pixels, also known as image objects), such that a set of segments will collectively cover the entire image, or a set of contours extracted from the image (Bücking T M, Hill E R, Robertson J L, Maneas E, Plumb A A, Nikitichev D I (2017) From medical imaging data to 3D printed anatomical models. PLoS ONE 12(5): e0178540. https://doi.org/10.1371/journal.pone.0178540; Mamta Juneja, Niharika Thakur, Dinesh Kumar, Ankur Gupta, Babandeep Bajwa, Prashant Jindal, Accuracy in dental surgical guide fabrication using different 3-D printing techniques, Additive Manufacturing, Volume 22, 2018, Pages 243-255).

At step 312, curve-fitting techniques are used to determine the anatomy of the globe of the eye. The curve fitting may be done manually or may be fully- or semi-automated. For example, on the 45 degree axial B-scan image obtained at step 302, 8-16 boundary points may be selected along the outline of the sclera. At least one boundary point may be selected in the macular region (e.g, the posterior portion of the eye). At least one boundary point may be selected at the equator of the eye. One or more boundary points may also be selected 1-2 mm anterior to the equator to ensure that the arms 106 are properly positioned and dimensioned. The remaining boundary points may be spaced equidistant in a range from 1-2 mm on the globe. After placement of the boundary points, a cubic spline interpolation technique may be used to fit a curve between each of the boundary points. The curve may satisfy the following equation:

$$S_n(x)=a_n x^3+b_n x^2=c_n x+d_n$$

By solving the system of n equations, where n is the number of boundary points selected (either manually or automatically), a cubic spline curve is obtained for the length of the indentor 100 (i.e., the anterior to posterior distance).

The curve formed using the axial B-scan image can be used to determine the curvature of the backbone 102 of the indentor 100. In some embodiments, the formed curve can be confirmed by A-scan imaging.

Similarly, on the transverse B-scan image obtained at step 306, boundary points may be positioned along the globe at the position at which the arms 106 will be positioned. For example, 5-10 boundary points may be positioned along the desired location of the arms 106. These boundary points may be selected manually or automatically by a computer. A cubic spline interpolation method can be used to connect the boundary points on the transverse B scan image. The two points that define the boundary of the curve can be used to determine the length and curvature of the arms 106. In some embodiments, the total length of the arms 106 may be in a range of 3-5 mm.

At step 314, the geometry of the indentor 100 is determined based on the anatomy of the eye, ascertained from the images acquired of the eye and the curve fitting described above. The two curves following the geometry of the globe of the eye (i.e., based on the axial and transverse B-scan images) are overlaid. Both curves are extruded in thickness and in width to generate the geometry of the backbone 102 and the arms 106 of the indentor 100. In some embodiments, the indentor 100 has a thickness range from 1-2 mm and width of the backbone 102 is between about 3 mm and about 6 mm. In some embodiments, the width of the backbone is between about 2 mm and about 7 mm.

The thickness and geometry of the raised pad 104 can be designed based on the clinical scenario. For example, the raised pad 104 may be semi-spherical with a radius of about 2-8 mm. The geometry of the raised pad 104 may be determined based on the ocular coherence tomography image quantifying the macular elevation.

Upon completion of the configured image-based design of the indentor 100, additive manufacturing (e.g., 3D printing, fused deposition modeling or direct metal laser sintering) may be used to manufacture the indentor 100. A silicone rubber covering may be added to coat the indentor 100. The indentor 100 may be sterilized prior to implantation. By manufacturing the indentor 100 using additive manufacturing, a configured indentor may be manufactured quickly and relatively inexpensively prior to implementation.

In various embodiments, a method of implanting the indentor 100 includes a making limited conjunctival peritomy at the superotemporal quadrant. The superior and temporal recti muscles are isolated. Tenon adhesions are cleared in the superotemporal quandrant. The indentor 100 is placed along the superotemporal quadrant and should fit along the natural curvature of the eye. The indentor 100 is sutured to the sclera with permanent sutures such as nylon or mersilene sutures along the backbone 102 and/or on the arms 106. Correct placement of the indentor 100 and indentation effect is verified by direct visualization and/or with indirect ophthalmoscopy. The conjunctiva is then closed with sutures.

Methods of Treatment

In some embodiments, this disclosure provides for a method of treating a patient having a macular disease, the method comprising attaching a macular indentor described herein to the eyeball of the patient.

As used herein, the term "patient" refers to a mammal having a macular disease. The mammal can be selected from a human, monkey, horse, rabbit, mouse, rat, pig, dog, or cat. In preferred embodiments, the patient is a human.

In some embodiments, the attachment occurs by suturing. In some embodiments, the attachment occurs by contacting a portion or all of the macular indentor with a surgical glue, then contacting the macular indentor to the eyeball and allowing the glue to set. In some embodiments, the surgical glue is selected from: ReSure Sealant (polyethylene glycol and trilysine acetate), cyanoacrylate, fibrin glue, Duraseal (polyethylene glycol ester and trilysine), Focalseal (polyethylene glycol acrylate and photoinitiator, cured by blue light), L-β-3,4-dihydroxyphenyl-β-alanine (DOPA), chondroitin sulfate reacting with glycidyl methacrylate, BioGlue (bovine albumin and glutaraldehyde), Progel (human albumin and a PEG crosslinker with two NHS activated ester groups), fibrin (Tisseel (Baxter Inc., Denmark), Evicel (Ethicon Inc., Bridgewater, NJ), Crosseal (OMRIX Biopharmaceuticals Ltd. Israel), and Hemaseel (Heamacure Corp., Canada)), Coseal (Cohesion Technologies, Inc., Palo Alto, CA) (PEG-based sealant, which is made of two 4-arm PEG with glutaryl-succinimidyl ester and thiol terminal groups), FocalSeal, and AdvaSeal (Ethicon Inc., Johnson & Johnson Medical KK).

In some embodiments, the macular disease is selected from: myopic tractional maculopathy, macular hole, myopic foveoschisis, myopic tractional maculopathy, posterior staphyloma and macular hole with retinal detachment. In some embodiments, the method further comprises confirming the proper placement of the macular indentor on the eyeball. The confirmation can be established by a method comprising OCT imaging of the retina.

In some embodiments, the macular indentor can further comprise a sterile fiber optic cable which can emit light at the tip of the fiber optic. The fiber optic cable (also referred to herein as "fiber optic" or "fiber optic fiber") can be removably connected to the backbone of the macular indentor. In some embodiments, the removable connection can be by way of tying the fiber optic cable to the indentor backbone by way of a suture. In some embodiments, the relative position of the tip of the fiber optic can be configured so as to be at or about at the same region as the bulb. The lighted tip will allow verification of the proper placement of the device to the macular region by viewing with an indirect ophthalmoscope during surgery. The fiber optic can be pulled out to extract the fiber optic after the implanted macular indentor is properly placed and sutured.

Systems

In some embodiments, this disclosure provides for a system for creating a patient-specific macular indentor, the system comprising:

(a) a computer unit which receives a first image of an eye of a patient, delineates the outline of a globe of the eye, develops a curve that matches the outline of the globe of the eye, and generates a geometry of a macular indentor such that a portion of the macular indentor follows the curve that matches the outline of the globe of the eye, and (b) an additive manufacturing device which creates an additively-manufactured macular indentor matching the generated geometry.

In some embodiments, the additive manufacturing device can be any of the AM-devices described herein. In some embodiments, the system further comprises a software file storing the data describing the geometry of the macular indentor. In some embodiments, the software file storing the data describing the geometry of the macular indentor can be recognized by the additive manufacturing device to construct a physical object of the designed macular indentor.

In some embodiments, the computer unit can perform operations in digital electronic circuitry, integrated circuitry, specially designed application specific integrated circuits (ASICs), field programmable gate arrays (FPGAs) computer hardware, firmware, software, and/or combinations thereof.

These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. In some embodiments, the eyeball images can be transmitted to the computer unit by the at least one input device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

In some embodiments, the computer program can be deployed to be executed on one computer or a plurality of computer or processing units at one site or distributed across multiple sites and interconnected by a communication network.

In some embodiments, the computer program used to perform the equations and methods described herein can further comprise writing a file. In some embodiments, a file can be a digital file, (e.g., stored on a hard drive, SSD, CD, or other tangible, non-transitory medium). A file can be sent from one device to another over the communication network as packets being sent from a server to a client.

Writing a file can comprise transforming a tangible, non-transitory computer-readable medium, for example, by adding, removing, or rearranging particles (e.g., with a net charge or dipole moment) into patterns of magnetization by read/write heads, the patterns then representing new collocations of information desired by, and useful to, the user. In some embodiments, writing involves a physical transformation of material in tangible, non-transitory computer readable media with certain properties such that magnetic read/write devices can then read the new and useful collocation of information. In some embodiments, writing a file comprises using flash memory such as NAND flash memory and storing information in an array of memory cells include floating-gate transistors. Methods of writing a file are well-known in the art and, for example, can be invoked automatically by a program from software or from a programming language.

Any of the electronic devices and/or components mentioned above in this system, with the associated interfaces, may be controlled and/or coordinated by operating system software, such as Windows OS (e.g. Windows XP, Windows 8, Windows 10, Windows Server, etc.), Windows CE, Mac OS, IOS, Android, Chrome OS, Unix, Linux, VxWorks, or other suitable operation systems. In other embodiment, the said electronics may be controlled by a proprietary operating system. Conventional operating systems control and schedule system processes for execution, perform memory management, provide file system, networking, I/O services, and provide an user interface functionality, such as a graphical user interface (GUI), among other systems and/or devices.

Additive Manufacturing Systems

The macular indentors of this disclosure can be constructed on any additive manufacturing system capable of manipulating metallic, semi-metallic, or alloyed materials. In some embodiments, additive manufacturing includes several different unique processes. Types of additive manufacturing processes include: laser engineered net shaping (LENS), directed light fabrication (DLF), direct metal deposition (DMD), and laser deposition (LD). Laser deposition in combination with rotational deposition allows for the production of metal compositional gradients radially from the center of a part by a process known as radial additive manufacturing (RAM) with functionally graded materials.

In some embodiments, the RAM process begins with a computer-generated model (CAD) as an input into a program that transforms the part's geometry into a programmable set of pathways that define the movement of the components within an additive manufacturing machine. The two main components of the additive manufacturing machine are a base and the nozzle. The part is constructed onto the base, and the nozzle is the component that utilizes the laser and material feed systems. Both the base and nozzle may be dictated by multiple-axis controls which allow for angular deposition, thereby removed the need for support material. The machine prints by feeding a continuous supply of metal or ceramic powder into the focal zone of a laser which melts the powder. The melted powder forms a melt pool and is deposited along the surface of the part as the laser moves along a predefined path. The melt pool quickly solidifies upon cooling so that the next layer may be added. Successive layers are printed until an entire part is produced. A 3-D CAD model of the conformal cooling molds described herein can be generated using AutoCAD, and converted into the appropriate file format for the additive-manufacturing system. The system can be a direct metal laser sintering (DMLS) powder bed 3-D printer. The build material can be titanium powder (CarTech® Puris Ti-6Al-4V Titanium Powder, Carpenter Technology Corp., USA). The additive manufacturing build instrument can be the EOS M 290 (EOS, Germany). The laser write speed can be varied and limited to a maximum of 7 meters per second. The laser can be a Yb-fiber laser operating at 400 W. The laser focus diameter is 100 microns. The step height can be varied between 20 to 40 microns.

EXAMPLES

Figure 6:
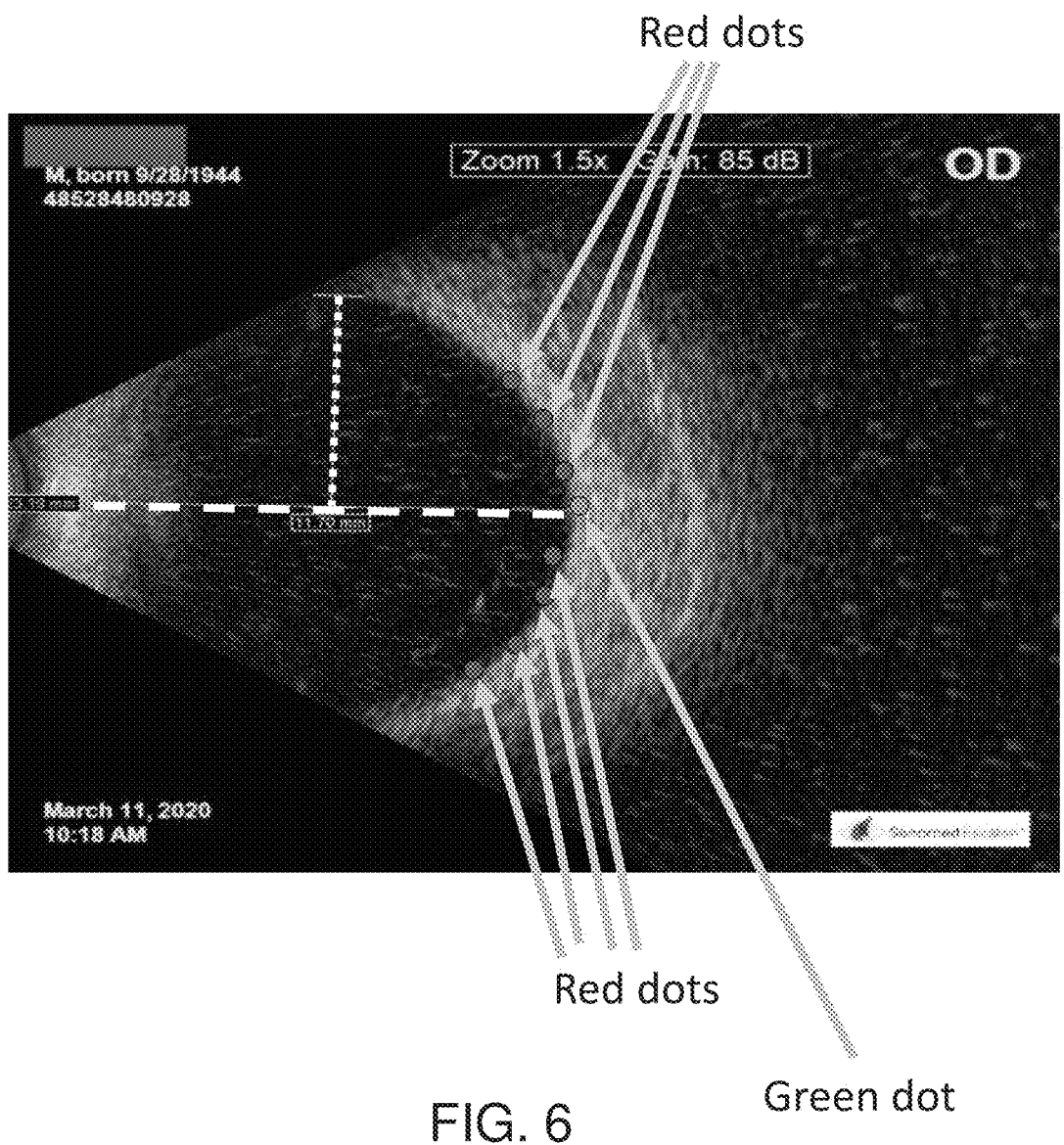
FIG. 6 shows ocular geometric parameters obtained from Coronal Bscan ultrasound imaging, including equatorial distance (dashed line) and axial distance (the shorter, and dotted line), a green point for the location of the cross section within the Sagittal scan, and a plurality of red points to indicate the curvature path the macular indentor device will follow (designated colored features indicated by arrows).
Figure 7:
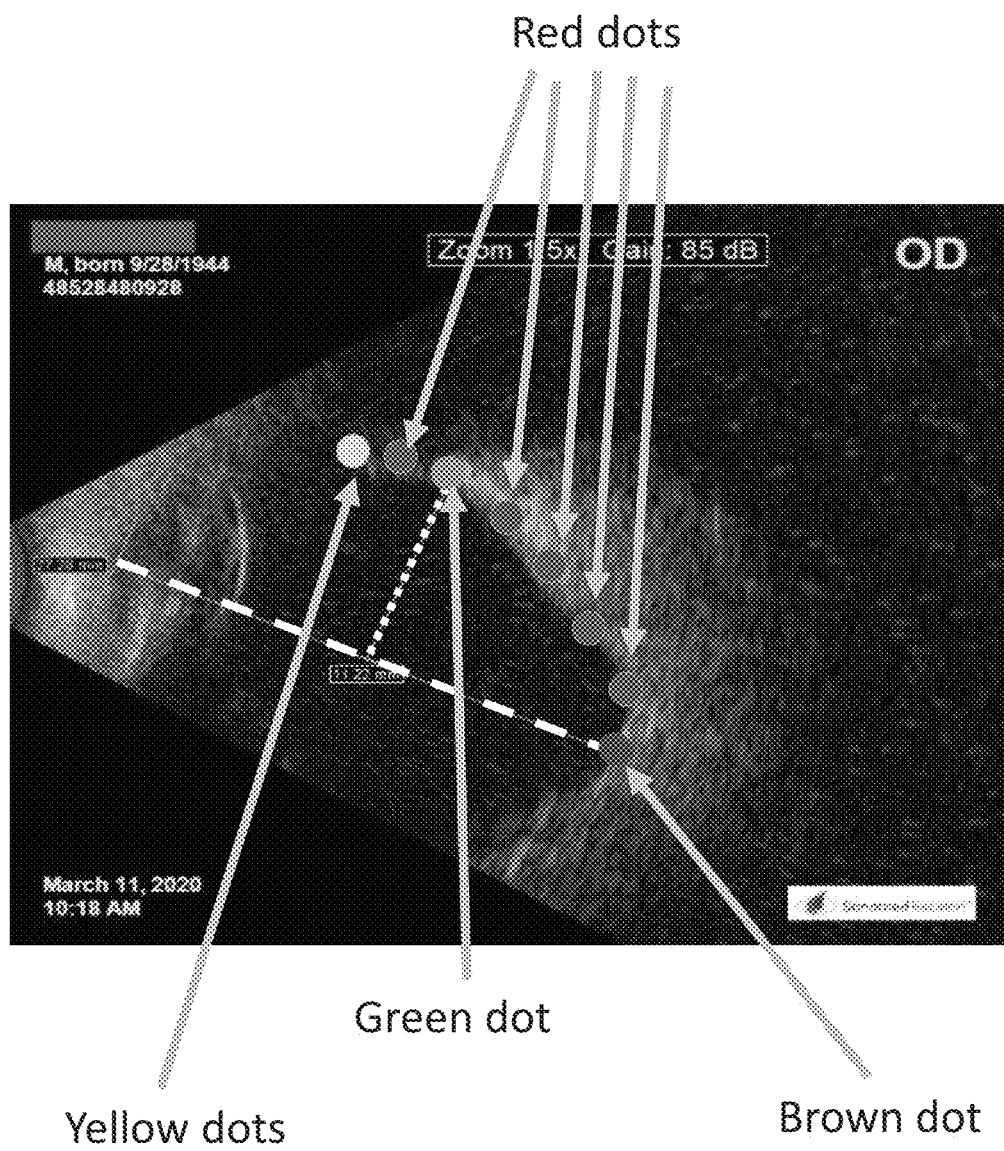
FIG. 7 shows ocular geometric parameters obtained from Sagittal Bscan ultrasound imaging, including the equatorial distance (dashed line) and axial distance (dotted line), a green point for the location of the cross section with the Sagittal scan, a yellow point to indicate the tip/end of the top cross, a brown point for the equatorial location (location of the center of the bulb), and a plurality of red points to indicate the curvature path the macular indentor device will follow. (designated colored features indicated by arrows).

Example 1. Method of Interpreting Scanned Ocular Features into Design of Macular Indentor for Additive Manufacture A method for creating a macular indentor made by 3-D printing (additive manufacturing) methods of this disclosure was performed from a rabbit eye model. First, coronal (FIG. 6) and sagittal (FIG. 7) Bscans were obtained. Ocular location points from each feature were identified as follows: from the coronal Bscan, the equatorial distance (in blue) and axial distance (in yellow) were obtained. Also, points were identified in the image, including a green point for the location of the cross section with the Sagittal scan, and a plurality of red points to indicate the curvature path the maclar indentor device should follow. From the sagittal Bscan, the equatorial distance (in blue) and axial distance (in yellow) was obtained. A green point for the location of the cross section with the Sagittal scan. A yellow point to indicate the tip/end of the top cross. A brown point for the equatorial location (location of the center of the bulb). A plurality of red points to indicate the curvature path the device will follow.

Figure 8:
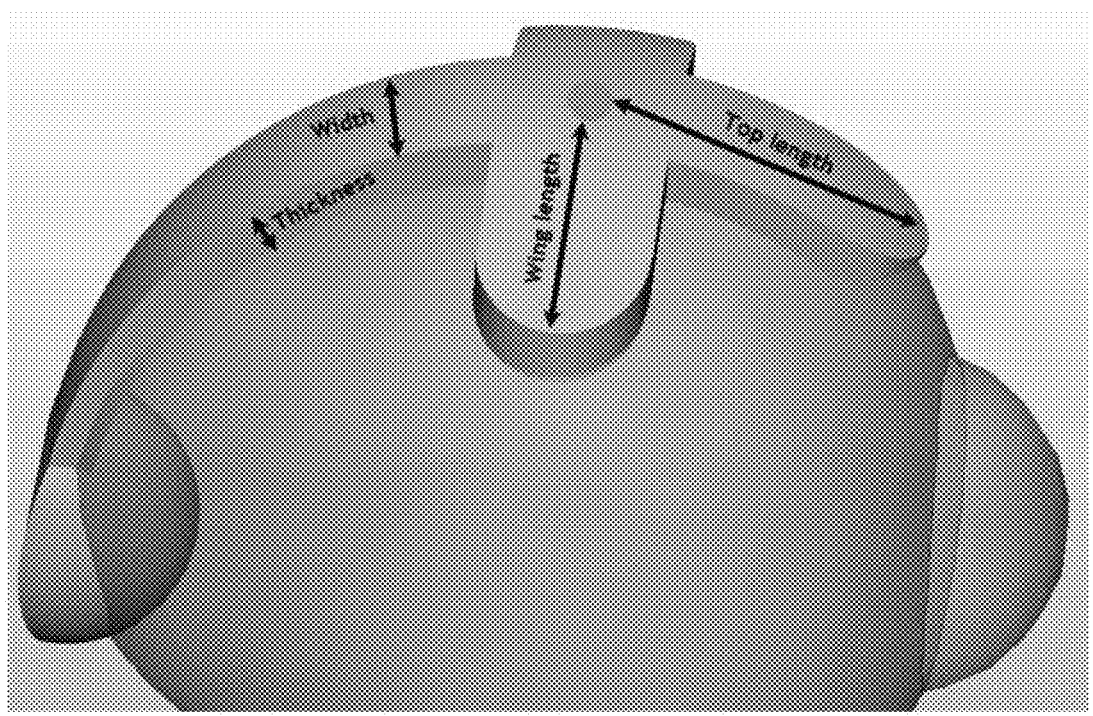
FIG. 8 shows the dimensions of a representative macular indentor of this disclosure, where the width of the device, and of the wings, are 4 mm, the thickness of the device is 1 mm, the top length as measured from the cross of the wings and spline is 7 mm to the end of the spline, and the wing length is 6 mm.

In the alternative, when scanned dimensions were not fully describing the ocular features of the patient, the following parameters were set for the macular indentor (FIG. 8): width of the macular indentor device—wings/backbone (4 mm, but can range from 2 to 6 mm in some embodiments), thickness of the device (1 mm, but can range from 0.2 to 2 mm in some embodiments), top length=7 mm (but can range from 5 to 9 mm in some embodiments), and the wing length=6 mm (but can range from 3 to 12 mm in some embodiments).

In the scans, "OD" means it was a scan of the right eye and "OS" was for the left eye.

Figure 9:
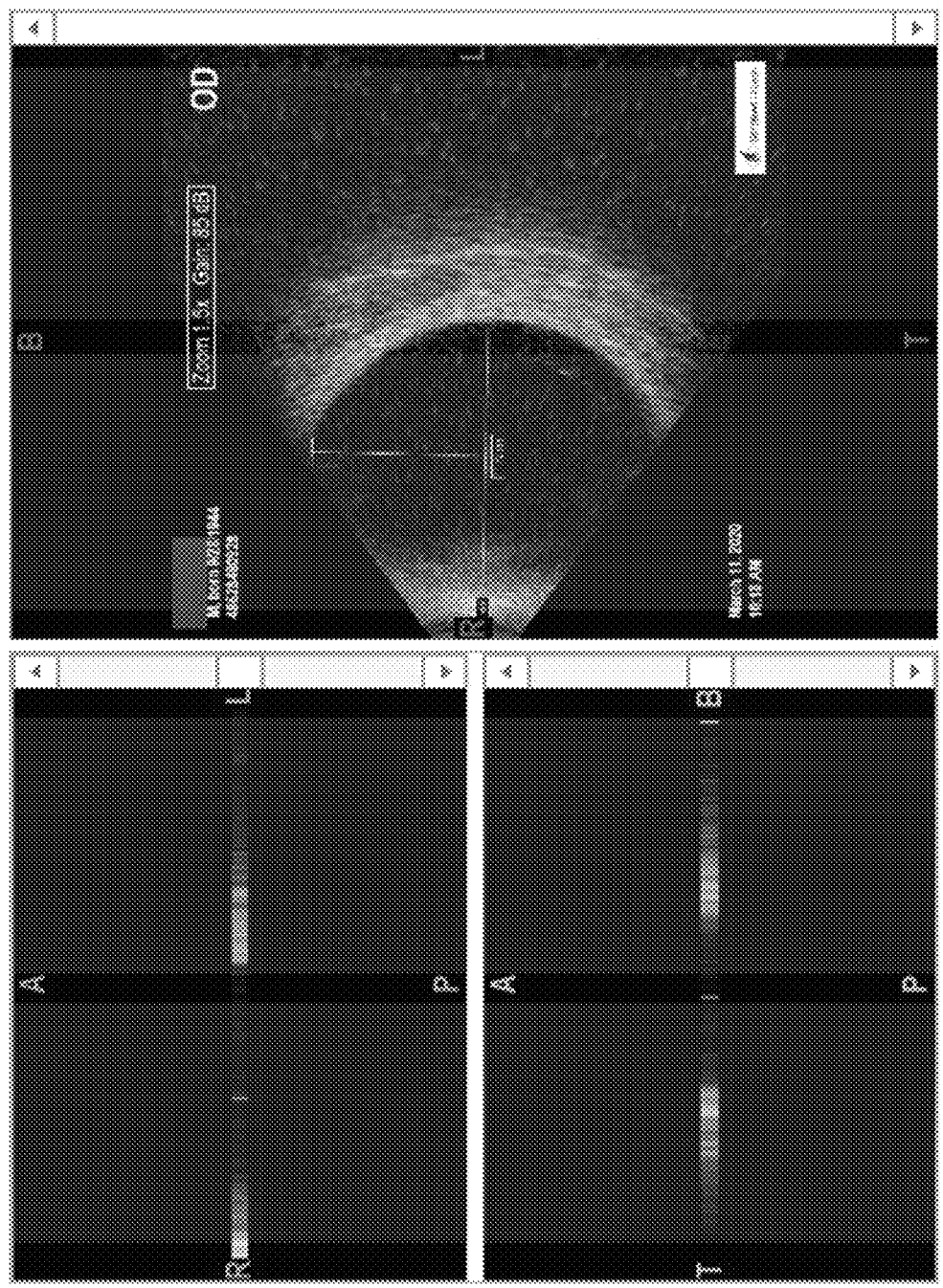
FIG. 9 shows the Coronal orientation of a Bscan of a model eye, wherein the image orientation is set for construction of the macular indentor.
Figure 10:
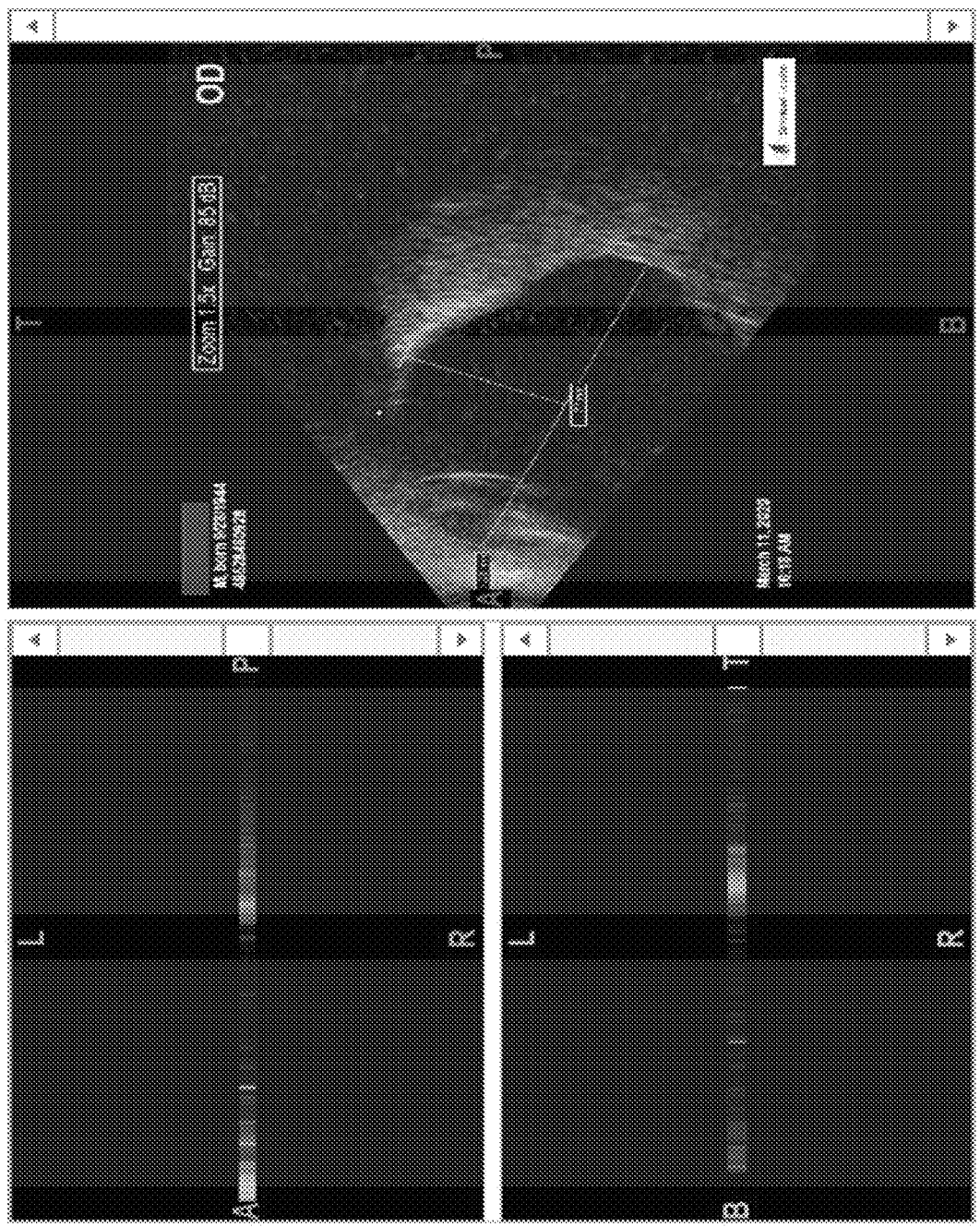
FIG. 10 shows the Sagittal orientation of a Bscan of a model eye, wherein the image orientation is set for construction of the macular indentor.
Figure 11:
FIG. 11 shows segmentation of the curvature of the eye and application of a spherical fit.
Figure 12:
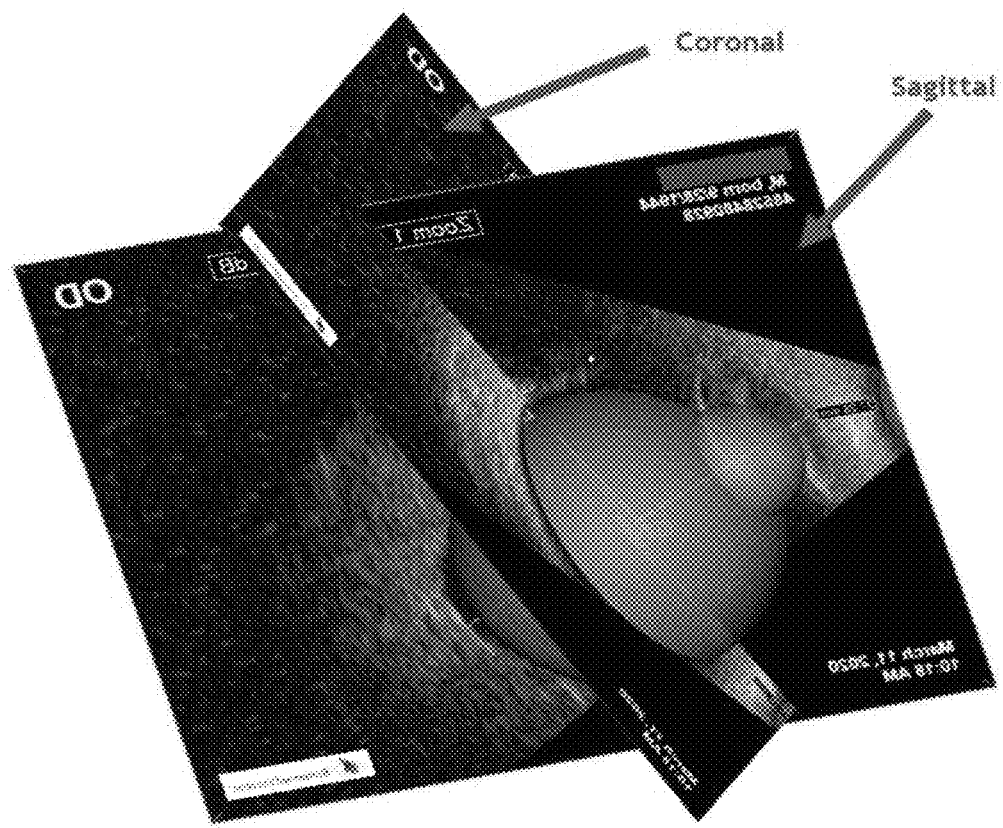
FIG. 12 shows the Coronal and Sagittal scans aligned at the common green point to describe a 3-D representation of the eye from the two scans.
Figure 13:
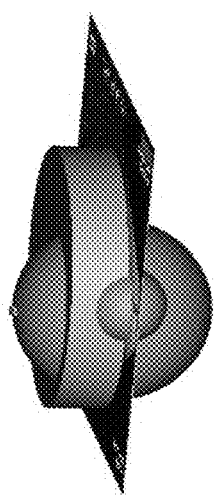
FIG. 13 shows a model of a created cylinder aligned to be perfectly matching the surface of the X-ray for each scan (Coronal, and Sagittal). Splines will be parallel to the curvature of the cylinder created for each scan.

The images were then imported into the Materialise Mimics Research software (Materialise, NV, Europe), using a 1×1×1 scan resolution. The equatorial distance on the 2D image was measured and divided (the original measurement percentage of the measured distance) to obtain the scan resolution required for the scaled import (isometric). The orientation of the imported images was depicted in FIG. 9 and FIG. 10. Next, the curvature of the eye was segmented and fit to a sphere (for easier visual alignment) (FIG. 11). Next, the two Bscans were aligned using the X-ray module of the software program, of the segmented eye, matching the common green point in both images (FIG. 12). In some embodiments, cylinders were created and aligned so as to be matching the surface of the X-ray for each scan (FIG. 13). In some embodiments, the splines will sit along the curvature of the created cylinders.

Figure 14:
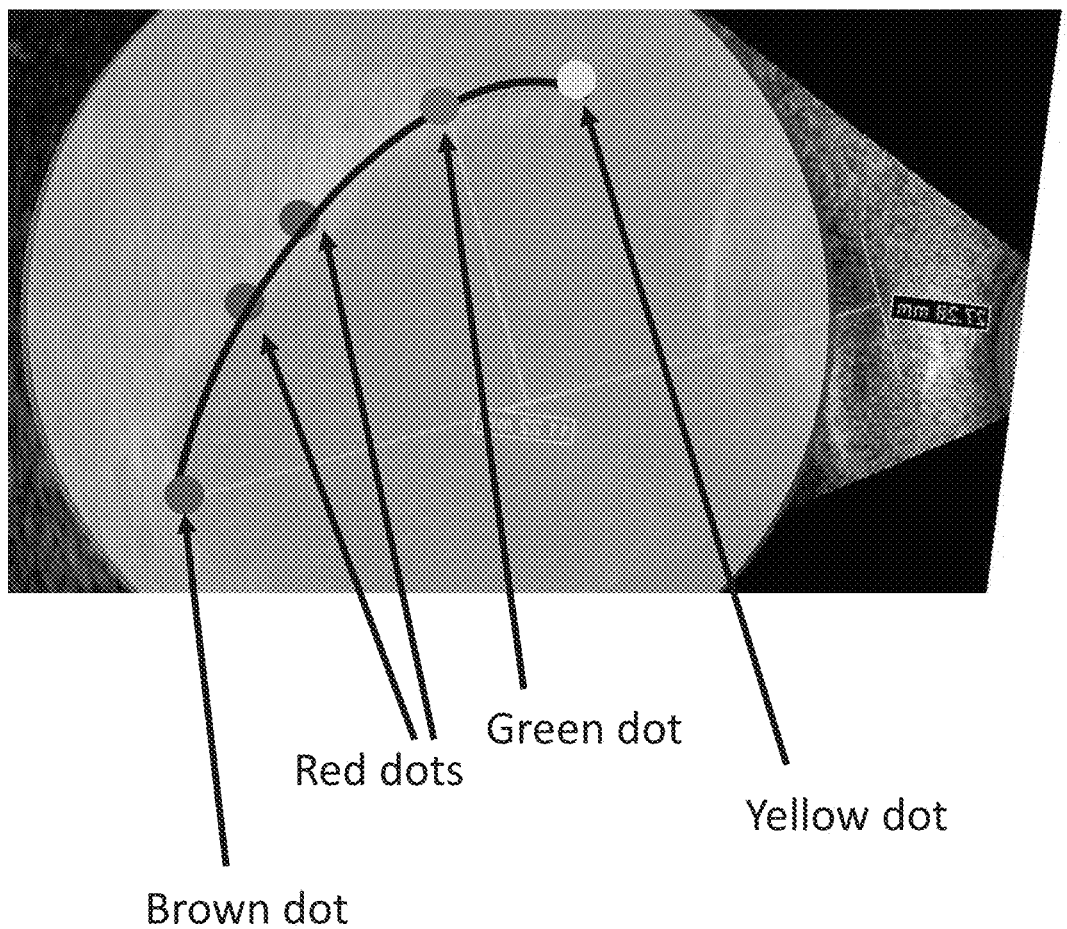
FIG. 14 shows a spline manually created using the points obtained from the ultrasound images. For the Sagittal scan, the location points (red dots) are interpolated to ensure the spline does not define a convex curvature, and only a smooth concave curve. The depicted color features are: the brown dot is the anchor/end of the spline, the yellow dot is the start of the spline, and the green dot is a point that must be true on the spline. (designated colored features indicated by arrows).

Next, a spline was created and overlayed using the points provided in the images. For the sagittal scan, interpolate the last few points to ensure there was no convex curvature, and only a smooth concave curve. The colored features in the images associated with geometric features are: the brown point was the anchor/end of the spline, the yellow point was the start of the spline, and the green point was a point that must be true on the spline (FIG. 14). The images were adjusted to align the green points to more closely overlap.

Figure 15:
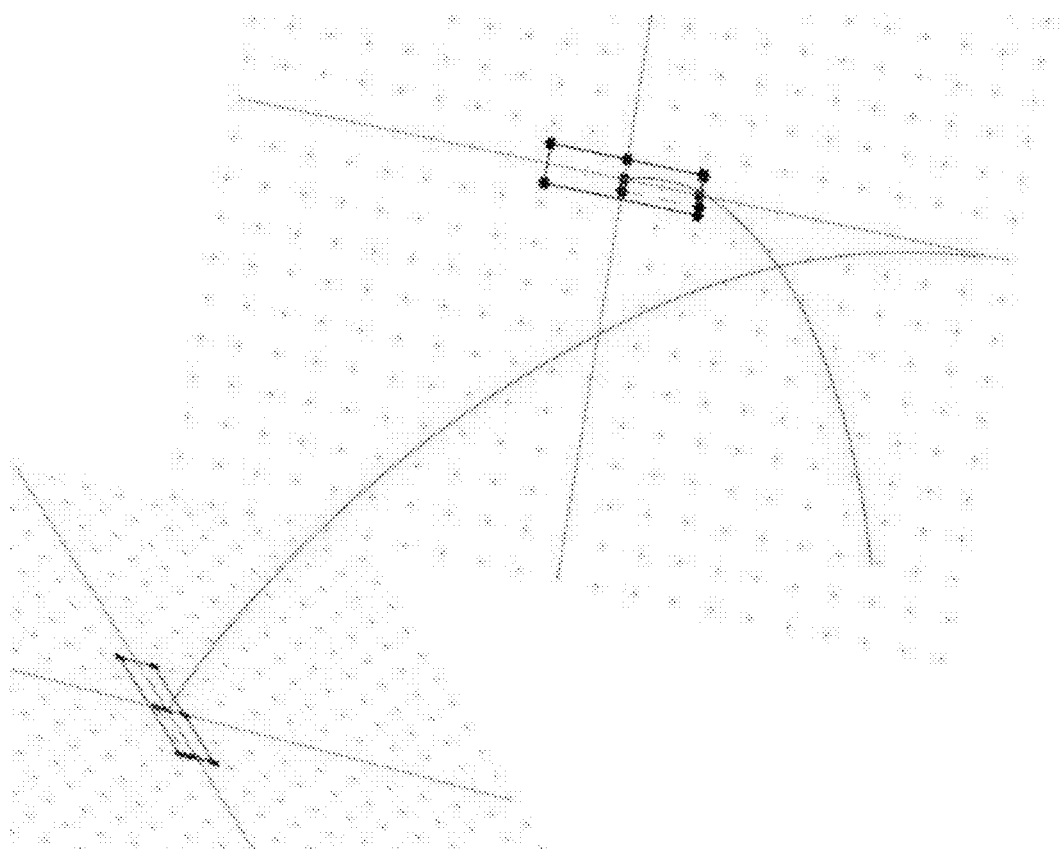
FIG. 15 shows a Materialise 3-Matic (Materialise, NV) imaging program image of splines created on the model, and establishing the width and thickness of the macular indentor.

Next, the splines were swept using the sketch tool within the software program to set the width and thickness (FIG. 15).

Figure 16A:
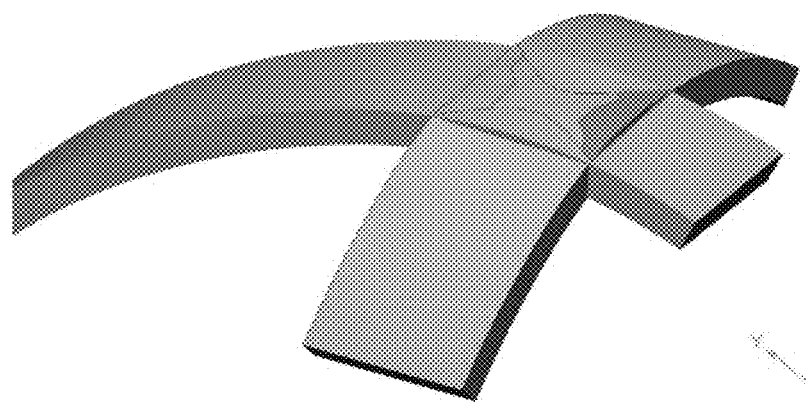
FIG. 16A shows the Boolean Union creation of surfaces created by the 3-Matic program, wherein the edges are marked and filled with hole freeform.
Figure 16B:
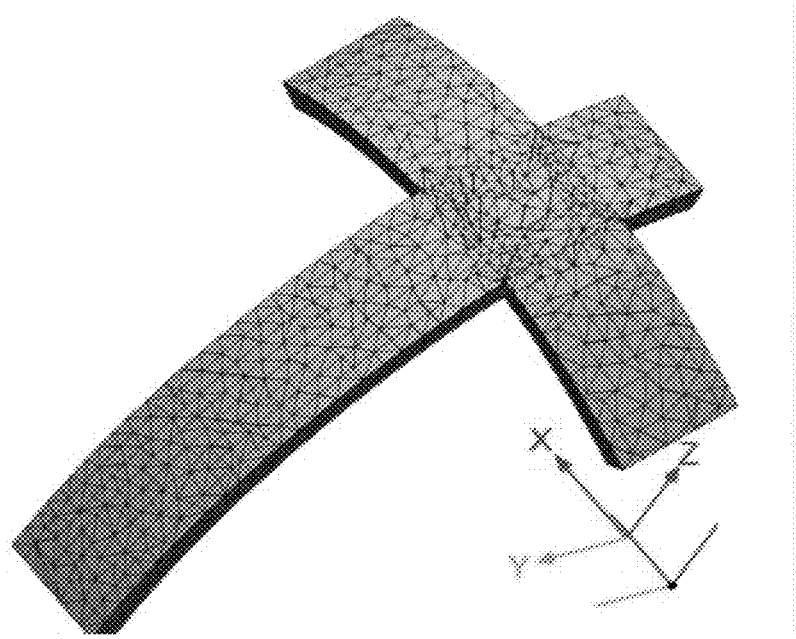
FIG. 16B shows the Boolean Union creation of surfaces by the 3-Matic program, wherein the surfaces are all remeshed and then smoothed to obtain smooth edge features.

A Boolean Union was then applied so as to separate the surfaces to be more uniform (mark and fill hole freeform on the edges) (FIG. 16A). The surfaces were then remeshed and smoothed to obtain a smoother edge (FIG. 16B). In some embodiments, the software operations were selected under the adaptive remesh options, and include: shape quality threshold (0.2165), maximum geometrical setting was 0.0200, control triangle edge was true, minimum triangle edge was 0.0000, maximum triangle edge was 1.000, number of iterations was 3, skip bad edges was false, preserve surface continuity was true, and preserve sharp edges was true.

Figure 17A:
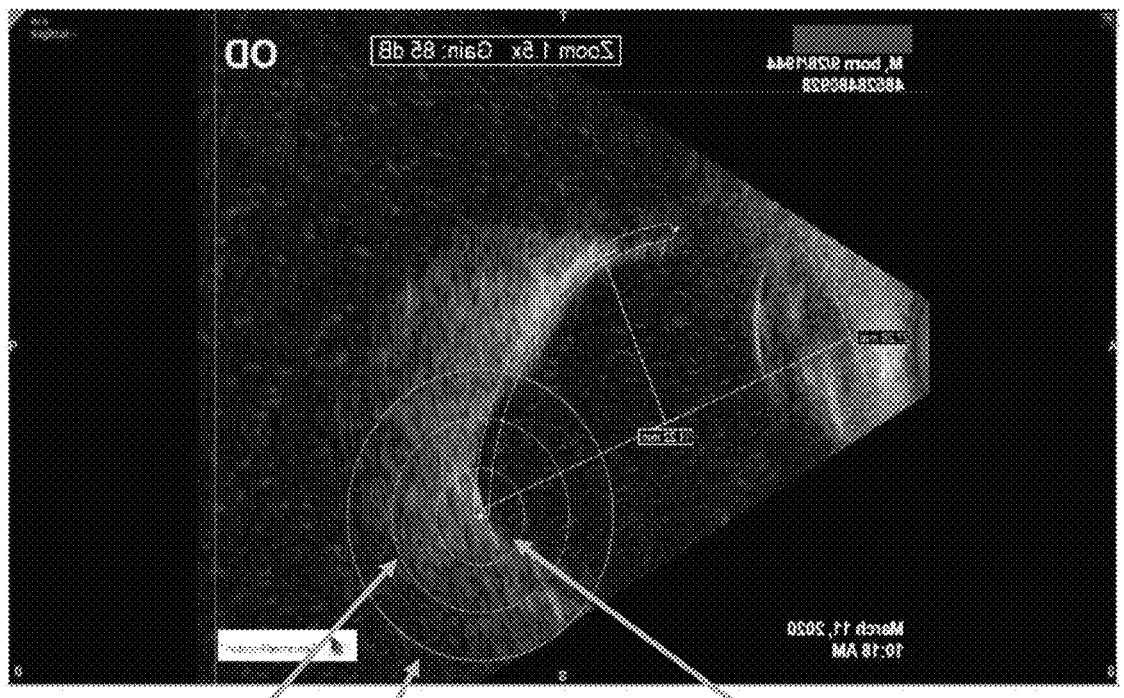
FIG. 17A shows the overlay of created potential bulb sizes on the Sagittal scan image to determine the optimal bulb size. The colored features are small Bulb (green circle (inner circle)): (20-25 mm axial length) set Radius to 3 mm; medium Bulb (orange circle (middle circle)): (25-30 mm) set radius to 6 mm; large Bulb (red circle (outer circle)): (>30 mm) set radius to 9 mm.
Figure 17B:
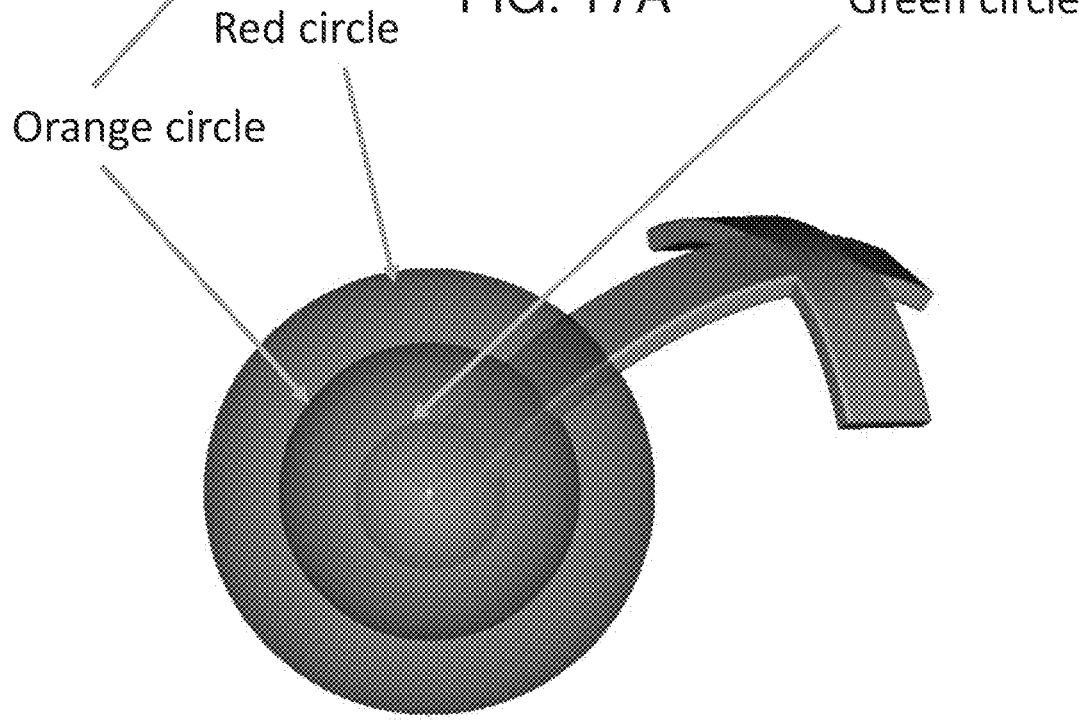
FIG. 17B shows a model of the overlap of potential bulb sizes with the cross part of the macular indentor.

Candidate bulb sizes were then created and overlayed on the sagittal Bscan (FIG. 17A). In some embodiments, the bulb size can range from 10 to 50 mm in diameter, and be a function of the axial scan distance. In some embodiments, the candidate bulb sizes comprise a radius of 3 mm (green circle in FIG. 17A) for 20-25 mm axial length, 6 mm (orange circle in FIG. 17A) for 25-30 mm axial length, and 9 mm (red circle in FIG. 17A) for over 30 mm axial length. The model of the selected bulb size was then combined with the model of the cross part of the macular indentor to visually confirm whether the curvature created for the cross was correct (e.g., the bulb will be large enough to compress a portion of the retina, but small enough such that the wings were sufficiently distanced from the bulb so as to not interfere with the compression of the bulb on the retina).

Figure 18:
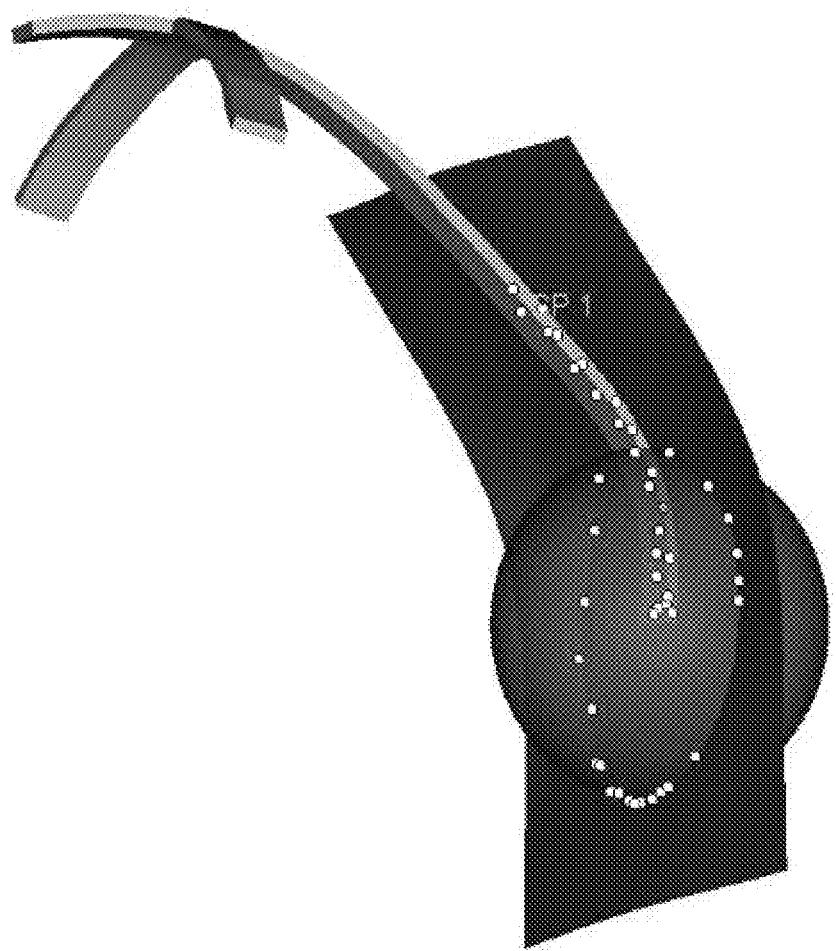
FIG. 18 shows a model of a sphere cut to match the curvature of the spline of the macular indentor.

Once the bulb size was determined, cut the sphere to match the curvature and to become an arc rather than a sphere (FIG. 18).

Figure 19:
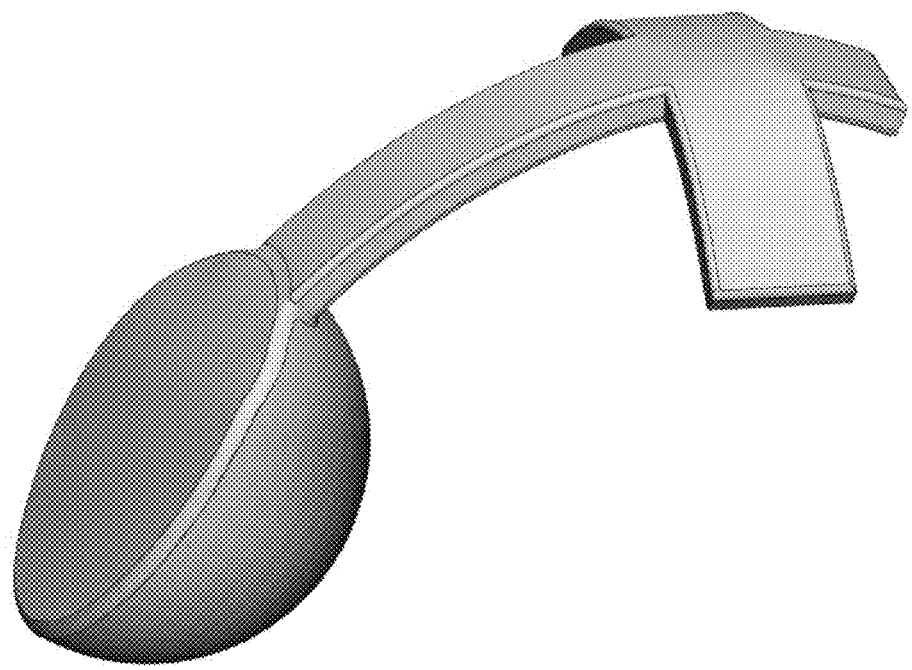
FIG. 19 shows a model of the merged parts with round edges of the macular indentor (the fillet radius is 0.2 mm).
Figure 20A:
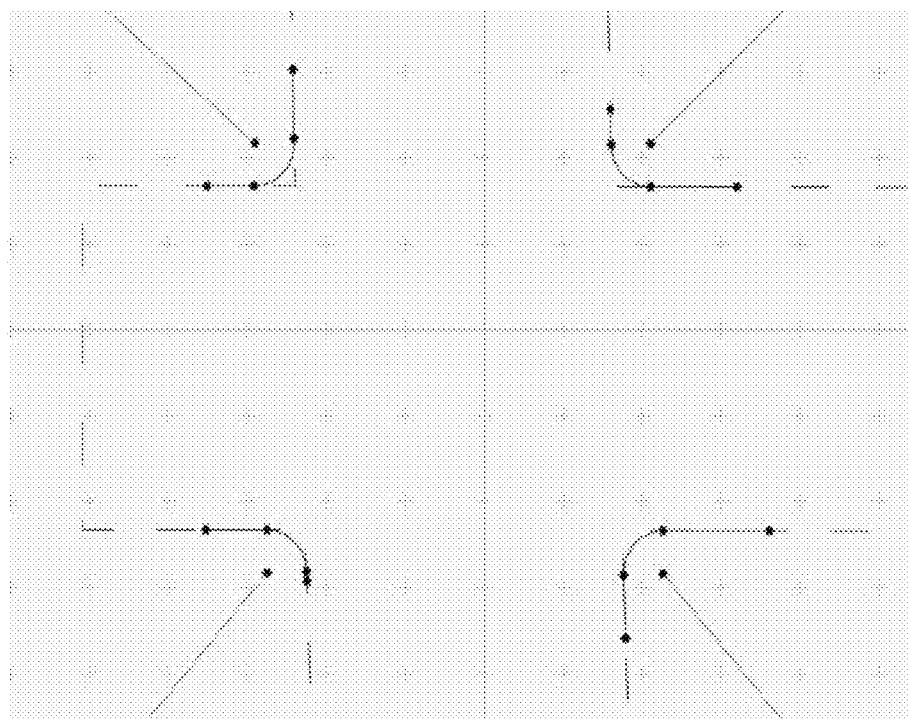
FIG. 20A shows a graphic of the wing-arm junction reconfigured to round the wing and arm (radius of curvature is 2 mm).
Figure 20B:
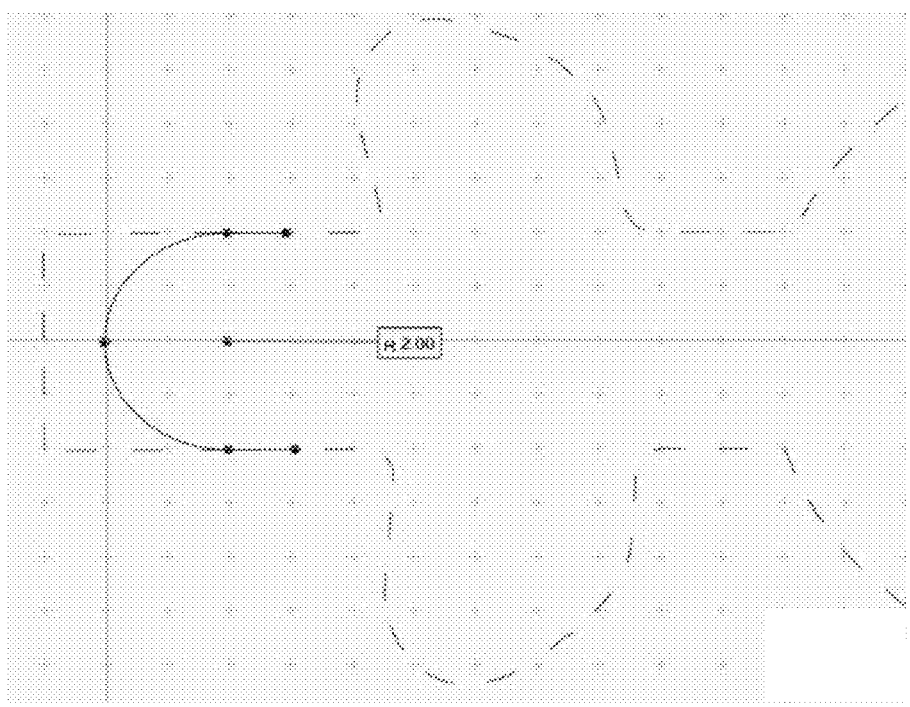
FIG. 20B shows a graphic of the arm edges reconfigured to round the arm edge (the tip is 2 mm, and the fillet radius is 0.5 mm).

The models of the parts were then merged and all edges were rounded (using a fillet radius of 0.2 mm in some embodiments) (FIG. 19). The sketch tool of the software was then used to round the wing-cross junctions (FIG. 20A), and of the wing-tip functions (FIG. 20B). The wing (R=2 mm), tip (R=2 mm) and "arm pits" (fillet radius=0.5 mm).

Figure 21A:
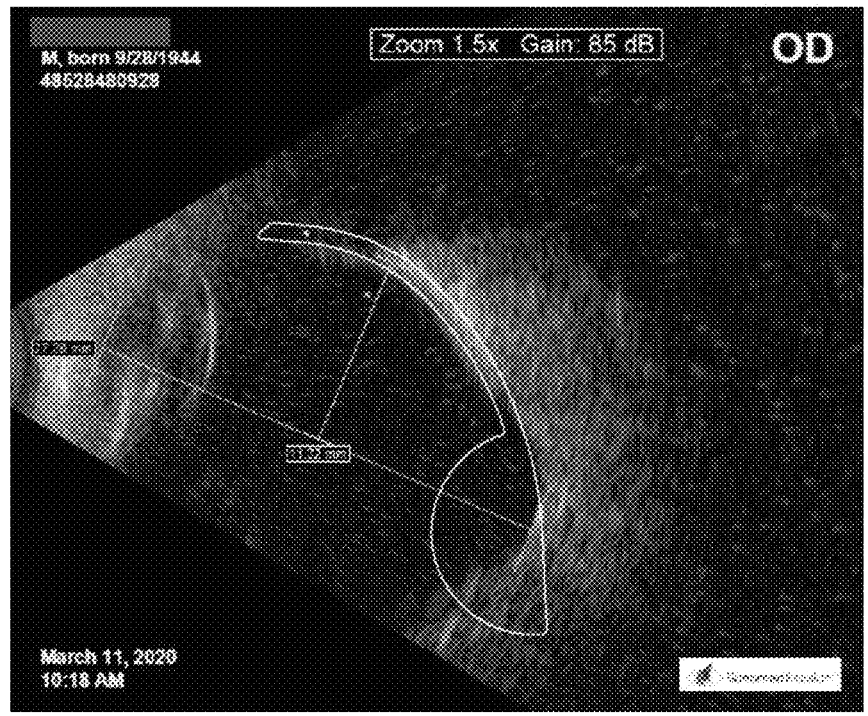
FIG. 21A shows a side view of a constructed model superimposed in a Saggital ultrasound image of a rabbit eye.
Figure 21B:
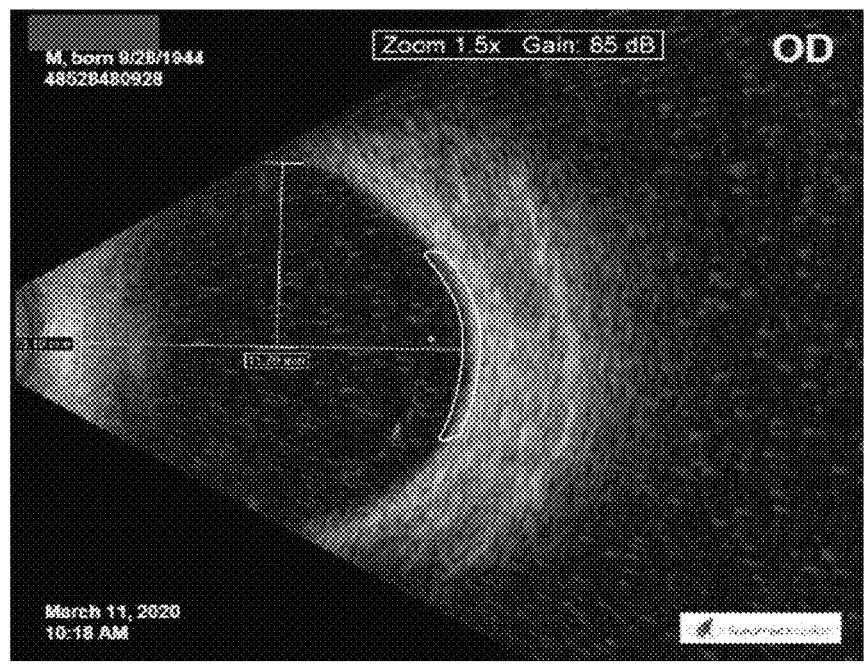
FIG. 21B shows a top view of a constructed model superimposed in a Saggital ultrasound image of a rabbit eye.
Figure 22:
FIG. 22 shows a titanium 3D-printed macular buckle of this disclosure fitted over a silicone model eye.

The edges were then rounded, remeshed, and smoothed (FIGS. 1A, 1B, 1C, 1D, and 1E). The macular indentor was then overlayed on the coronal (FIG. 21A) and sagittal (FIG. 21B) Bscans to confirm the appropriateness of the fit to the measured dimensions of the patient's eyeball. The model was then exported as an STL file for use in additive manufacture of one embodiment of the macular indentor of this disclosure. (FIG. 22).

Example 2. Implantation and In Vivo Imaging of Implanted Macular Indentor

The macular indentor made by the method described in Example 1 was implanted onto the eyeball of an anaesthetized male New Zealand White Rabbit (2.5 kg) which had been previously imaged by A-scan and B-scan ultrasonography to design and create a macular indentor configured to fit the eyeball of the patient.

Figure 23:
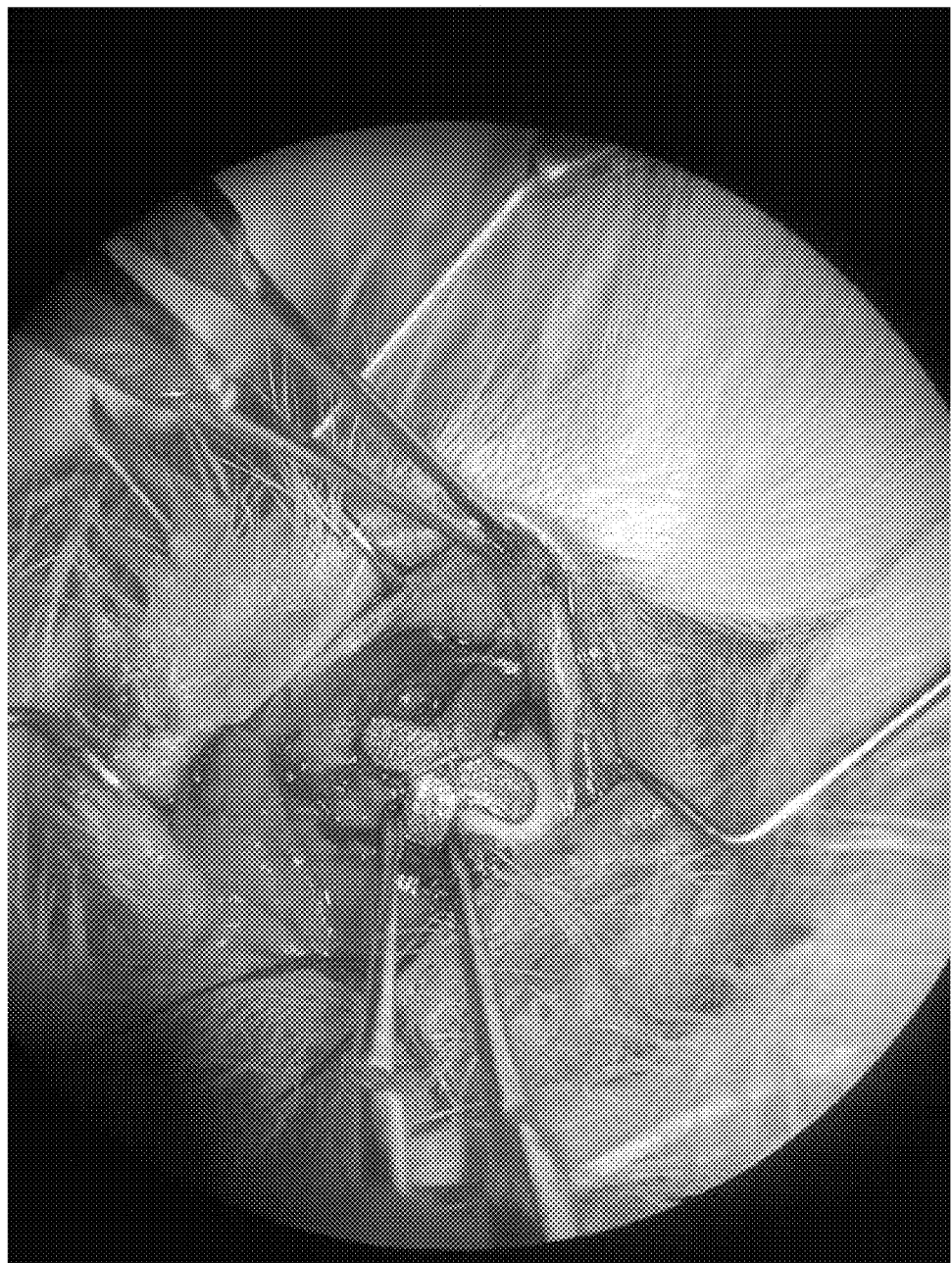
FIG. 23 is a photograph of a representative macular indentor of this disclosure implanted in the superotemporal quadrant of a rabbit eye. The macular indentor was secured with a X-stitch fashion with a 5-O Mersilene suture at the center of the cross and along the long arm of the macular indentor. The macular indentor was then covered with the conjunctiva and the conjunctiva was sutured close with a 7-O Vicryl suture.

As shown in FIG. 23, the macular indentor was implanted in the superotemporal quadrant of a rabbit eye. The macular indentor was secured with a X-stitch fashion with a 5-O Mersilene suture at the center of the cross and along the long arm of the macular indentor. The macular indentor was then covered with the conjunctiva and the conjunctiva was sutured close with a 7-O Vicryl suture.

Figure 24A:
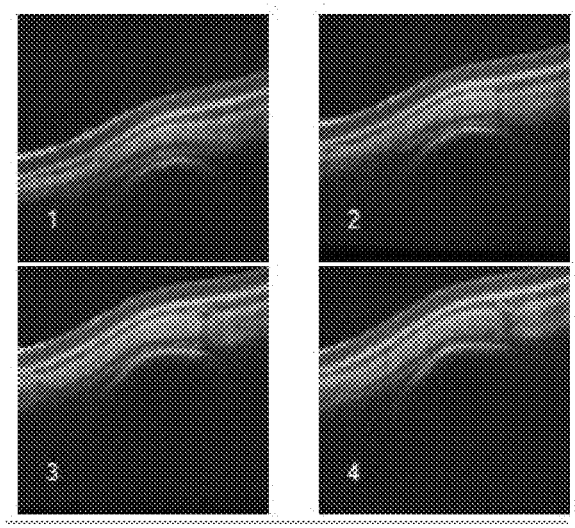
FIG. 24A shows multiple OCT (Optical coherence tomography) images of the eyeball of a patient (rabbit, as described herein) showing indentation of the posterior pole created by the device one week after implantation showing the circular indentation of the macula from the indentor. Note that rabbits do not have a fovea, so the indentation in the image is solely from the implanted macular indentor. (Images taken with ZEISS CIRRUS 5000 OCT Instrument, which was also used to take the B-scan and A-scan images described herein) (S=Superior region, I=Inferior region, T=inferotemporal region, N=inferonasal region; scan angle is 0 degrees, spacing between line rasters was 0.25 mm; total length of scan was 6 mm). OS image.
Figure 24B:
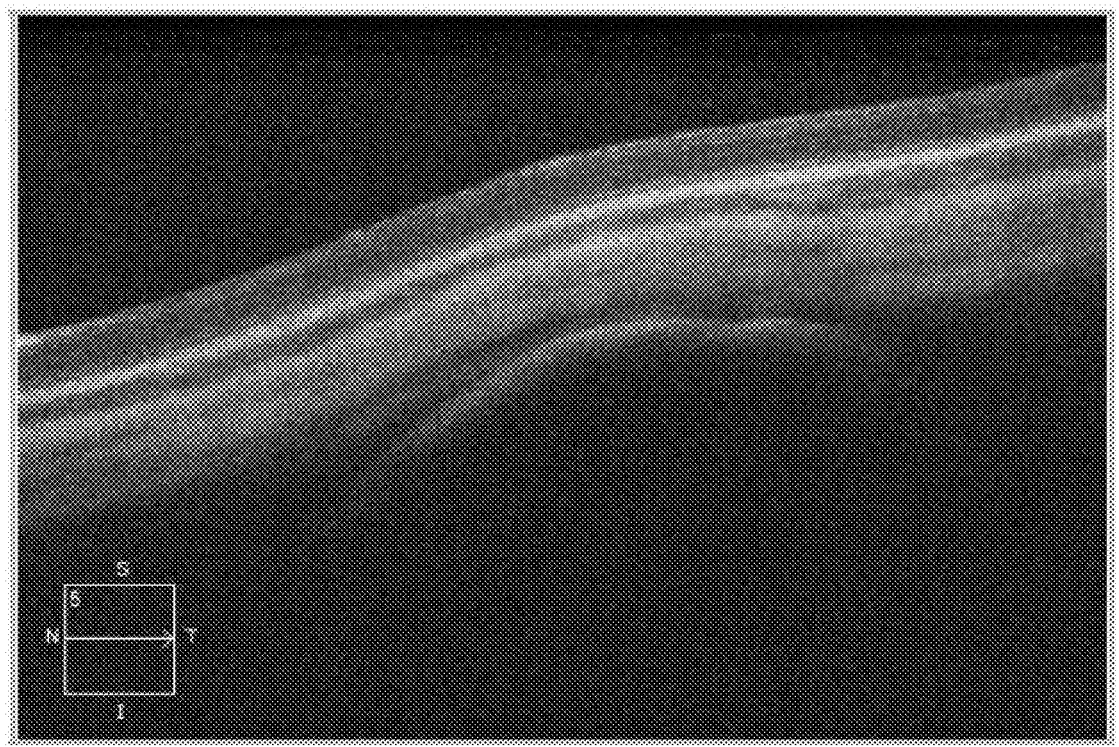
FIG. 24B shows an expanded view of a selected OCT image, indicating the features of the retina conforming to the shape of the embedded macular indentor.

As shown in FIG. 24A and FIG. 24B, OCT (Optical coherence tomography) images demonstrate indentation of the posterior pole created by the device one week after implantation showing the circular indentation of the macula from the indentor. Note that rabbits do not have a fovea, so the indentation in the image is solely from the implanted macular indentor. (Images taken with ZEISS CIRRUS 5000 OCT Instrument, which was also used to take the B-scan and A-scan images described herein) (S=Superior region, I=Inferior region, T=inferotemporal region, N=inferonasal region; scan angle is 0 degrees, spacing between line rasters was 0.25 mm; total length of scan was 6 mm). OS image.

Example 3. Additional Imaging Methods to Confirm Placement of Implanted Macular Indentor In some embodiments, the impact of the macular indentor can be further confirmed with fundus imaging which will demonstrate the shape and position of the macular indentor bulb on the retina.

In some embodiments, the macular indentor can further comprise a sterile lighted fiber optic that is retractable after implantation. The lighted tip will allow verification of the proper placement of the device to the macular region by viewing with an indirect ophthalmoscope during surgery. The fiber optic can be tied with a vicryl suture to the backbone of the device and can simply be pulled out after the implant is properly placed and sutured. In some embodiments, the fiber optic can be coated with a lubricant (e.g., polyethylene glycol, MW 500 to 50,000) to make the fiber optic extraction more facile.

The preceding merely illustrates the principles of various embodiments of the disclosure. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

All numbers expressing quantities or parameters used in the specification are to be understood as additionally being modified in all instances by the term "about". Notwithstanding that the numerical ranges and parameters set forth, the broad scope of the patient matter presented herein are approximations, the numerical values set forth are indicated as precisely as possible. For example, any numerical value may inherently contain certain errors, evidenced by the standard deviation associated with their respective measurement techniques, or round-off errors and inaccuracies.

I claim:

1. A macular indentor for implantation on an eye of a patient, the macular indentor comprising:
   a curved backbone extending from a first end to a second end, the curved backbone comprising an inner scleral-contacting concave face extending from said first end to said second end, the inner scleral-contacting concave face of the curved backbone having a geometry configured to match a geometry of the eye and is sized and configured to be secured to a sclera of the eye; and
   a raised pad coupled to the first end of the curved backbone and extending inward from the inner scleral-contacting concave face of the backbone and toward the macula of the eye such that, when the macular indentor is implanted on the eye, the raised pad applies localized pressure to the sclera of the eye which contacts the macula of the eye; and
   a pair of arms extending from the second end of the backbone in opposite directions such that the arms and the second end of the backbone form a cross shape, wherein the pair of arms are sized and configured to be secured to the sclera of the eye;
   wherein the pair of arms extend orthogonally to a midline of the curved backbone;

wherein an aperture extends through intersection of arms with midline of the curved backbone, the aperture configured to receive a suture to secure the macular indentor to the eye;

wherein the eye further comprises a macular detachment having a height, and the raised pad is sized and configured to match the height of the macular detachment;

wherein the raised pad is sized and configured to correct refractive error caused by foveoschisis, myopic tractional maculopathy, macular hole, myopic tractional maculopathy, posterior staphyloma, and macular hole with retinal detachment.

2. The macular indentor of claim 1, wherein the macular indentor is constructed from at least one material selected from the group consisting of: titanium, cobalt, nylon, Teflon (polytetrafluoroethylene), polyurethane, high density polyethylene (HDPE), polypropylene, and stainless steel.

3. The macular indentor of claim 1, wherein the macular indentor is coated with a silicone covering.

4. The macular indentor of claim 1, wherein the backbone further comprises a width which is between about 2 mm and about 7 mm.

5. The macular indentor of claim 1, wherein a cross-section of the raised pad is semi-spherical and is configured to create a semi-spherical indentation of the macula.

6. The macular indentor of claim 1, further comprising a sterile lighted optic fiber that is removably attached to the backbone.

* * * * *